(12) United States Patent
Heinz et al.

(10) Patent No.: US 8,715,999 B2
(45) Date of Patent: May 6, 2014

(54) FLAVIVIRIDAE MUTANTS COMPRISING A DELETION IN THE CAPSID PROTEIN FOR USE AS VACCINES

(75) Inventors: Franz X. Heinz, Vienna (AT); Christian Mandl, Vienna (AT); Petra Schlick, Vienna (AT); Andreas Meinke, Pressbaum (AT)

(73) Assignee: Valneva Austria GmbH, Vienna (AT)

( * ) Notice: Subject to any disclaimer, the term of this patent is extended or adjusted under 35 U.S.C. 154(b) by 569 days.

(21) Appl. No.: 12/866,631

(22) PCT Filed: Feb. 6, 2009

(86) PCT No.: PCT/EP2009/051351
§ 371 (c)(1),
(2), (4) Date: Aug. 6, 2010

(87) PCT Pub. No.: WO2009/098277
PCT Pub. Date: Aug. 13, 2009

(65) Prior Publication Data
US 2010/0323003 A1     Dec. 23, 2010

(30) Foreign Application Priority Data

Feb. 8, 2008 (EP) .................................... 08101404

(51) Int. Cl.
*C12N 7/04* (2006.01)
*C12N 15/86* (2006.01)

(52) U.S. Cl.
USPC ........................................ 435/236; 435/320.1

(58) Field of Classification Search
None
See application file for complete search history.

(56) References Cited

U.S. PATENT DOCUMENTS

| 8,486,419 B2 * | 7/2013 | Heinz et al. | ................ | 424/205.1 |
| 2002/0164349 A1 | 11/2002 | Weiner et al. | .............. | 424/186.1 |

FOREIGN PATENT DOCUMENTS

| EP | 1 018 558 | 7/2000 |
| WO | WO 02/066621 | 8/2002 |
| WO | WO 2004/016794 | 2/2004 |

OTHER PUBLICATIONS

Bhuvanakantham and Ng, "Analysis of self-association of West Nile virus capsid protein and the crucial role played by Trp 69 in homodimerization," *Biochem. Biophys. Res. Commun.*, 329:246-55, 2005.
Björklund et al., "Molecular characterization of the 3' noncoding region of classical swine fever virus vaccine strains," *Virus Genes*, 16:307-12, 1998.
Butrapet et al., "Attenuation markers of a candidate dengue type 2 vaccine virus, strain 16681 (PDK-53), are defined by mutations in the 5' noncoding region and nonstructural proteins 1 and 3," *J. Virol.*, 74:3011-3019, 2000.
Dokland et al., "West Nile virus core protein; tetramer structure and ribbon formation," *Structure*, 12:1157-63, 2004.
Guirakhoo et al., "Recombinant chimeric yellow fever-dengue type 2 virus is immunogenic and protective in nonhuman primates," *J. Virol.*, 74:5477-85, 2000.
Hall et al., "Loss of dimerisation of the nonstructural protein NS1 of Kunjin virus delays viral replication and reduces virulence in mice, but still allows secretion of NS1," *Virology*, 264:66-75, 1999.
Hope et al., "Sequence motifs required for lipid droplet association and protein stability are unique to the hepatitis C virus core protein," *J. Gen. Virol.*, 81:1913-25, 2000.
Khromykh et al., "RNA binding properties of core protein of the flavivirus Kunjin," *Arch. Virol.*, 141:685-99, 1996.
Lai et al., "Evaluation of molecular strategies to develop a live dengue vaccine," *Clin. Diagn. Virol.*, 10:173-9, 1998.
Ma et al., "Solution structure of dengue virus capsid protein reveals another fold," *Proc. Natl. Acad. Sci. USA*, 101:3414-9, 2004.
Mandl et al., "Attenuation of tick-borne encephalitis virus by structure-based site-specific mutagenesis of a putative flavivirus receptor binding site," *J. Virol.*, 74:9601-9, 2000.
Mandl et al., "Spontaneous and engineered deletions in the 3' noncoding region of tick-borne encephalitis virus: construction of highly attenuated mutants of a flavivirus," *J. Virol.*, 72:2132-40, 1998.
Markoff et al., "A conserved internal hydrophobic domain mediates the stable membrane integration of the dengue virus capsid protein," *Virology*, 233:105-117, 1997.
McMinn, "The molecular basis of virulence of the encephalitogenic flaviviruses," *J. Gen. Virol.*, 78:2711-22, 1997.
Meyers et al., "Mutations abrogating the RNase activity in glycoprotein E(rns) of the pestivirus classical swine fever virus lead to virus attenuation," *J. Virol.*, 73:10224-35, 1999.
Nitayaphan et al., "Nucleotide sequence of the virulent SA-14 strain of Japanese encephalitis virus and its attenuated vaccine derivative, SA-14-14-2," *Virology*, 177:541-52, 1990.
Patkar et al., "Functional requirements of the yellow fever virus capsid protein," *J. Virol.*, 81:6471-81, 2007.
Post et al., "Heterogeneity in envelope protein sequence and N-linked glycosylation among yellow fever virus vaccine strains," *Virology*, 188:160-7, 1992.
Schlick et al., "Helices alpha2 and alpha3 of West Nile virus capsid protein are dispensable for assembly of infectious virions," *J. Virol.*, 83:5581-91, 2009.
Xie et al., "Mutation in NS5 protein attenuates mouse neurovirulence of yellow fever I7D vaccine virus," *J. Gen. Virol.*, 79:1895-9, 1998.

\* cited by examiner

*Primary Examiner* — Michael Burkhart
(74) *Attorney, Agent, or Firm* — Wolf, Greenfield & Sacks, P.C.

(57) ABSTRACT

The present invention relates to a mutant virus of the family flaviviridae, comprising a deletion in the capsid protein of at least 20 successive amino acids, without any further deletion, substitution or insertion mutation except of the amino acids next to the deletion, which may be substituted.

34 Claims, 12 Drawing Sheets

TBE Virus

WN Virus

Den Virus Typ 2

FIG.1A

CSF Virus

BVD Virus

BD Virus

FIG. 1B

Figure 3:
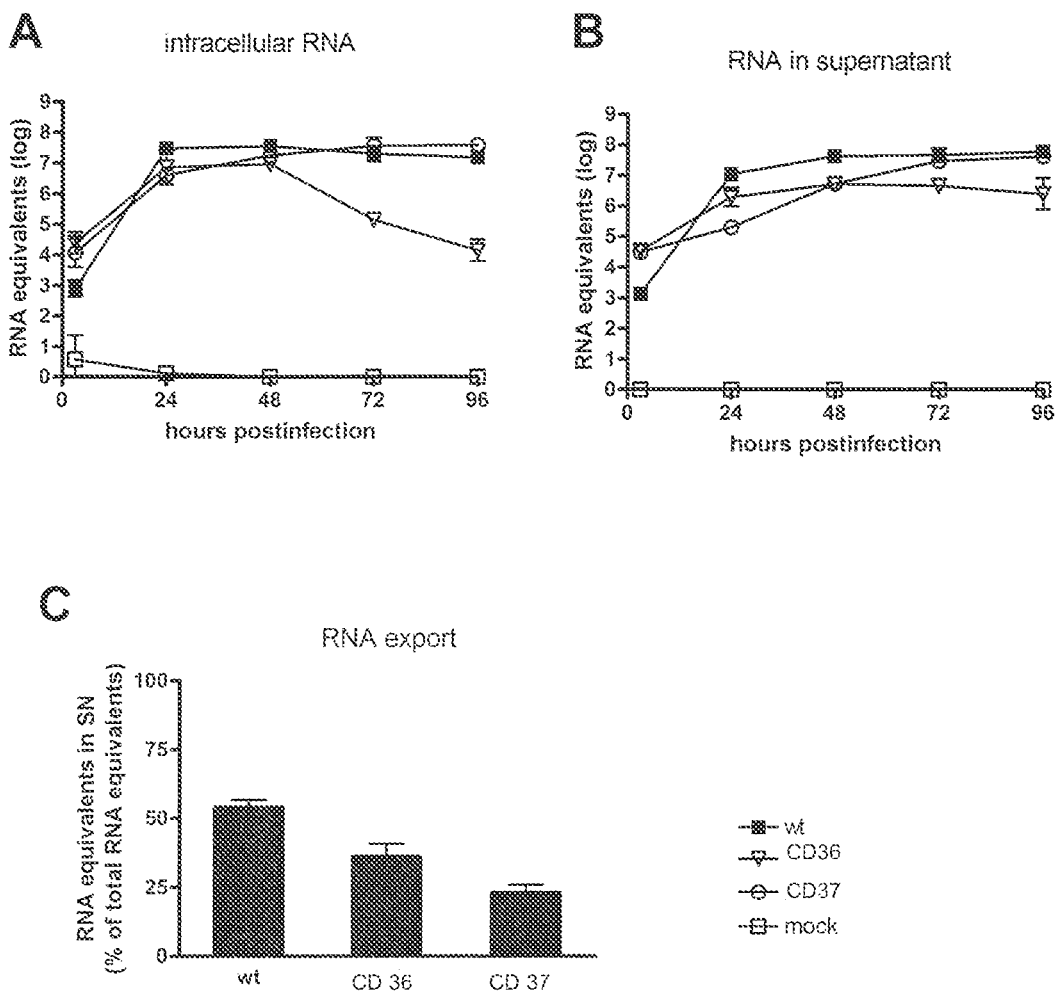
Figure 3:
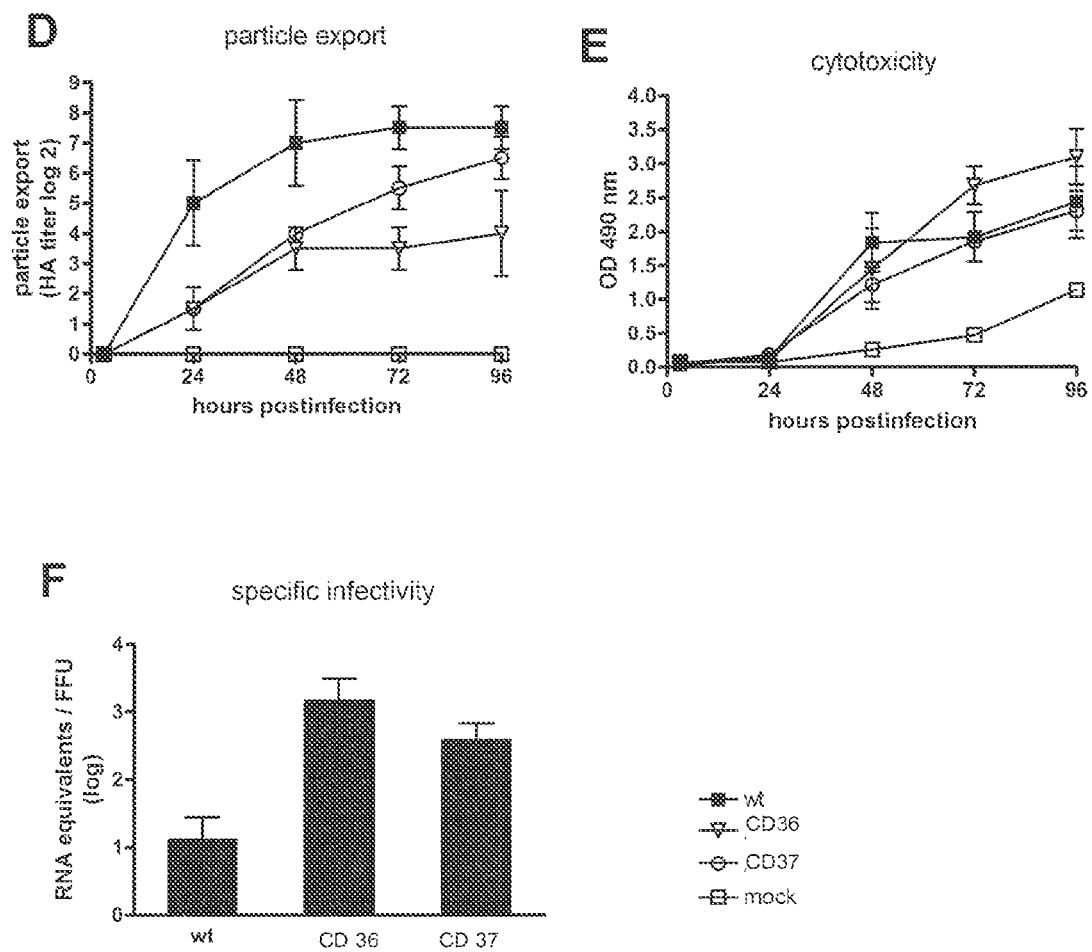

HC Virus Typ 1
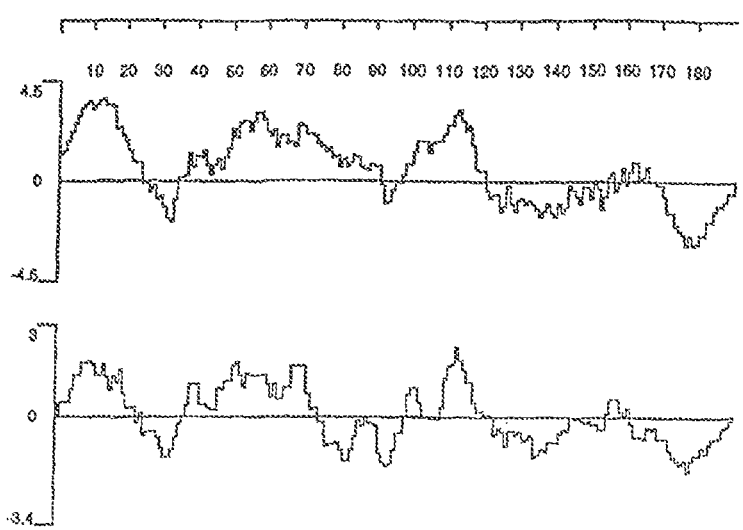
HC Virus Typ 2
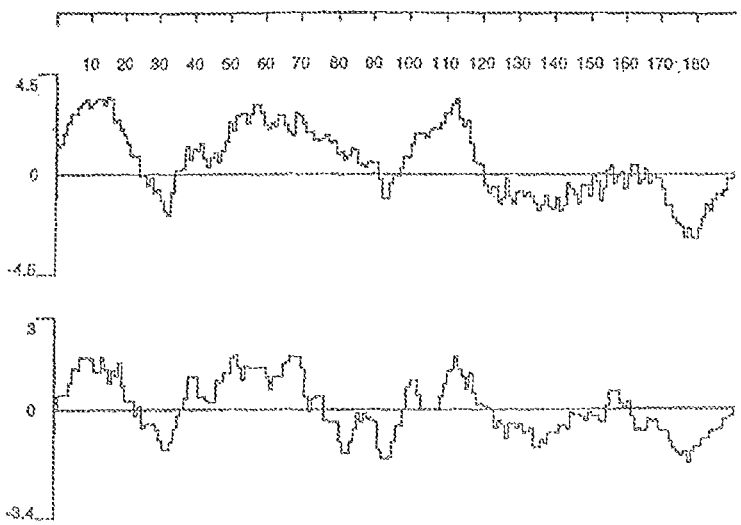
HC Virus Typ 3
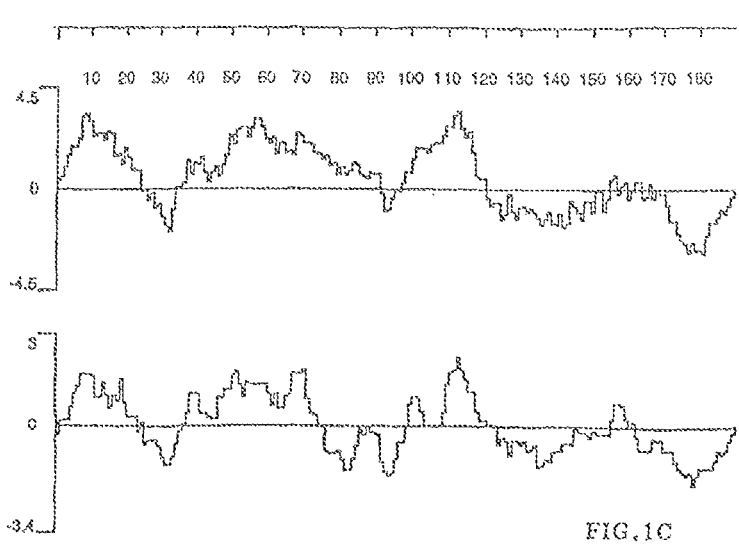
FIG.1C

FIG. 2

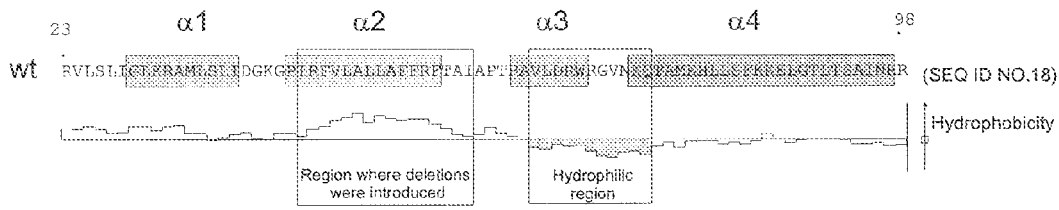
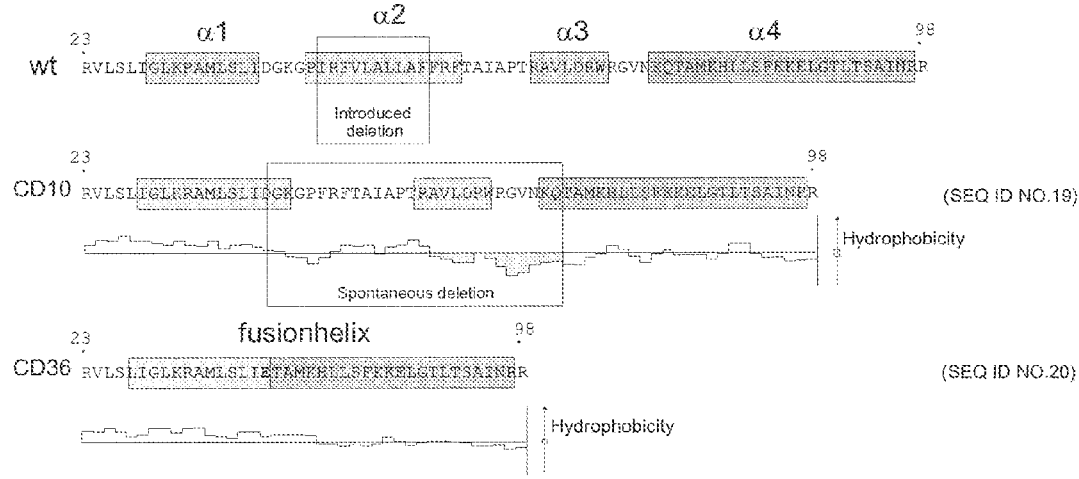
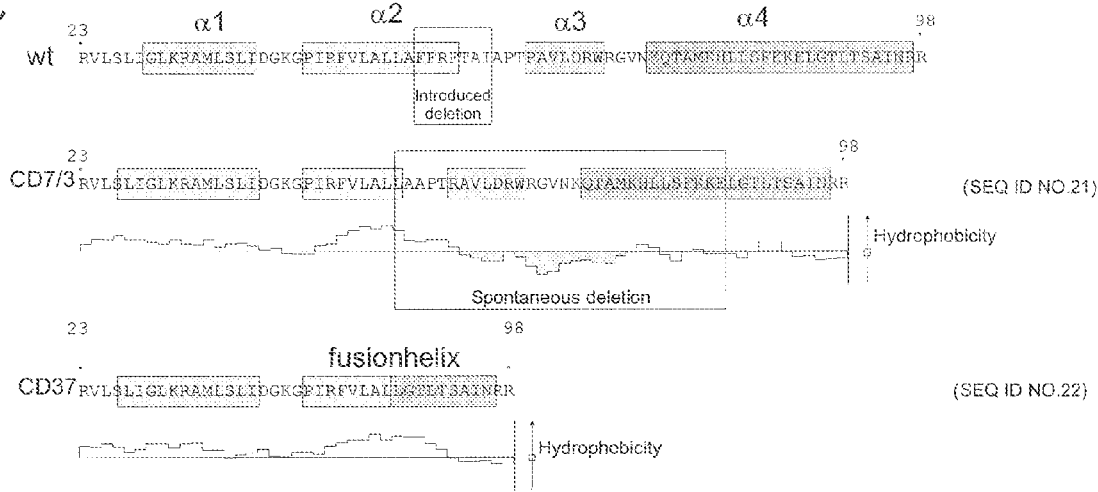
Fig. 4

Fig. 5A
WNV, Kunjin subtype (SEQ ID NO.10)
```
              α1                 α2                α3          α4
Conf: 975068799998976558865399999999999972688898999983006756799999
Pred: CCCCHHHHHHHHHHHHCCCCHHHHHHHHHHHHHCCCCHHHHHHHHCCCHHHHHHHH
  AA: RVLSLTGLKRAMLSLIDGRGPTRFVLALLAFFRFTAIAPTRAVLDRWRSVNKQTAMKHLL
              .         .         .         .         .         .
              30        40        50        60        70        80

α4
Conf: 8899999999996259
Pred: HHHHHHHHHHHHHCC
  AA: SFKKELGTLTSAINRR
              .
              90
```

Fig. 5B
WNV NY99 (SEQ ID NO.11)
```
                                            α1          α2
Conf: 98889999840034654101021056310567767734623379999999999843788
Pred: CCCCCCCCCCCCHHHHCCCHHCCCCHHHHHHHHHHCCCCHHHHHHHHHHHHHCCCC
  AA: MSKKPGGPGKSRAVNMLKRGMPRVLSLIGLKRAMLSLIDGKGPIRFVLALLAFFRFTAIA
              .         .         .         .         .         .
              10        20        30        40        50        60

α3              α4
Conf: 688999871458989999999999999999999997203237888704999999999998
Pred: CCHHHHHHHCCCCHHHHHHHHHHHHHHHHHHHHHHCCCCCCCCCHHHHHHHHHHHH
  AA: PTRAVLDRWRGVNKQTAMKHLLSFKKELGTLTSAINRRSSKQKKRGGKTGIAVMIGLIAS
              .         .         .         .         .         .
              70        80        90        100       110       120

Conf: 519
Pred: HCC
  AA: VGA
       .
       123
```

Fig. 5C
WNV CD 7/3 (SEQ ID NO.12)
```
                                      α1          α2          α3
Conf: 988899998655210000010103721569998787634755446877661588999999
Pred: CCCCCCCCCCCCCCEEHHCCCHHCCCHHHHHHHHHHCCCCHHHHHHHHCCCCHHHHH
  AA: MSKKPGGPGKSRAVNMLKRGMPRVLSLIGLKRAMLSLIDGKGPIRFVLALLAAPTRAVLD
                                                            52/60
              α4
Conf: 8244788899999999899999999999983356010279
Pred: HHCCCCHHHHHHHHHHHHHHHHHHHHCCCCHHCCC
  AA: RWRGVNKQTAMKHLLSFKKELGTLTSAINRRSSKQKKR
```

Fig. 5D
WNV CD37 (SEQ ID NO.13)

```
                                                     α1                α2 + α4
Conf: 98788999867400022210110157547799999898655876489999999999799999
Pred: CCCCCCCCCCCCEEHHHHHCCCCCCCHHHHHHHHHHHCCCCHHHHHHHHHHHHHHHHHH
  AA: MSKKPGGPGKSRAVNMLKRGMPRVLSLIGLKRAMLSLIDGKGPIRFVLALLGTLTSAINR
                                                             50/88

Conf: 86431569
Pred: HHHHCCCC
  AA: RSSKQKKR
```

Fig. 5E
WNV CD10 (SEQ ID NO.14)

```
                                        α1                        α3
Conf: 98788999841002222001343284401789999998343011001248328999 9722
Pred: CCCCCCCCCCCCHHHHHCCCHHHCCCCHHHHHHHHHHHHCCCCCCCCCCCHHHHHHHC
  AA: MSKKPGGPGKSRAVNMLKRGMPRVLSLIGLKRAMLSLIDGKGPFRFTAIAPTRAVLDRWR
                                                          43/54
            α4
Conf: 4787789999999989999999999973122232179
Pred: CCCHHHHHHHHHHHHHHHHHHHHHHHCCCHHHCCC
  AA: GVNKQTAMKHLLSFKKELGTLTSAINRRSSKQKKR
```

Fig. 5F
WNV CD36 (SEQ ID NO.15)

```
                                                α1+α4
Conf: 9878899986621355430101167879899998540499999999986999999999972
Pred: CCCCCCCCCCCCHHHHHCCCCCCCCHHHHHHHHHHHHHHHHHHHHHHHHHHHHHHHHHH
  AA: MSKKPGGPGKSRAVNMLKRGMPRVLSLIGLKRAMLSLIETAMKHLLSFKKELGTLTSAIN
                                                             39/76

Conf: 121454129
Pred: CCHHHHHCC
  AA: RRSSKQKKR
```

Fig. 5G
WNV CD48 (SEQ ID NO.16)

```
                                       α1+α4
Conf: 98889998812457775215002553487999975312077899998531114 4129
Pred: CCCCCCCCCHHHHHHHHCCCCCCCCHHHHHHHHHHHHHHHHHHHHHHHHHHHHHHCC
  AA: MSKKPGGPGKSRAVNMLKRGMPRVLSLIGLKRAMLSLIELGTLTSAINRRSSKQKKR
                                     39/88
```

Fig. 5H
WNV CD48duplication (SEQ ID NO.17)

```
                                   α1+α4                  α1ext.
Conf: 987889998774002232014543257269999999999999961554113035 4432778
Pred: CCCCCCCCCCCCCHHHHHHHHHHHHHCCCCHHHHHHHHHHHHHHHHCCCCCCCHHHHHHHHH
  AA: MSKKPGGPGKSRAVNMLKRGMPRVLSLIGLKRAMLSLIELGTLTSAMLKRGMPRVLSLIG
                    16                         39/88    94/16

α1+α4
Conf: 9999962999999999972002454129
Pred: HHHHHHHHHHHHHHHHHHHCCHHHHHCC
  AA: LKRAMLSLIELGTLTSAINRRSSKQKKR
            39/88     94
```

Alignment WNV NY99 and WNV, Kunjin subtype

```
(SEQ ID NO.18) WNV NY99   RVLSLIGLKRAMLSLIDGKGPIRFVLALLAFFRFTAIAPTRAVLDRWRGVNKQTAMKHLL
               Cons.      RVLSL GLKRAMLSLIDG+GP RFVLALLAFFRFTAIAPTRAVLDRWR VNKQTAMKHLL
(SEQ ID NO.10) Kunjin     RVLSLTGLKRAMLSLIDGRGPTRFVLALLAFFRFTAIAPTRAVLDRWRSVNKQTAMKHLL
                               .    .    .    .    .    .    .
                              23   30   40   50   60   70   80

WNV NY99..SFKKELGTLTSAINRR 294
               Cons.     SFKKELGTLTSAINRR
               Kunjin    SFKKELGTLTSAINRR 76
                              .    .
                             90   98
```

Fig. 6A

Alignment WNV NY99 and Dengue Virus 2

```
(SEQ ID NO.23) WNV NY99   NMLKRGMPRVLSLIGL-KRAMLSLIDGKGPIRFVLALLAFFRFTAIAPTRAVLDRWRGVN
               Cons.      NMLKR  RV ++ L KR  L ++ G+GP++ +AL+AF RF  I PT +L RW  +
(SEQ ID NO.24) Dengue     NMLKRERNRVSTVQQLTKRFSLGMLQGRGPLKLFMALVAFLRFLTIPPTAGILKRWGTIK
                               .    .    .    .    .    .    .
                              15   20   30-  40   50   60   70

WNV NY99  KQTAMKHLLSFKKELGTLTSAINRR
               Cons.     K  A+  L  F+KE+G + +  +NRR
               Dengue    KSKAINVLRGFRKEIGRMLNILNRR
                              .    .    .
                             80   90   98
```

Fig. 6B

US 8,715,999 B2

FLAVIVIRIDAE MUTANTS COMPRISING A DELETION IN THE CAPSID PROTEIN FOR USE AS VACCINES

This application is a national phase application under 35 U.S.C. §371 of International Application No. PCT/EP2009/051351 filed 6 Feb. 2009, which claims priority to European Application No. 08101404.5 filed 8 Feb. 2008. The entire text of each of the above-referenced disclosures is specifically incorporated herein by reference without disclaimer.

The invention relates to mutated flaviviridae for vaccines.

The family Flaviviridae comprises three genera, the genus flaviviruses, the genus pestiviruses, and the genus hepaciviruses.

The genus flaviviruses mainly includes viruses transmitted by mosquitoes or ticks, many of which are important pathogens of humans, and also of animals. Particularly important are the yellow fever (YF) virus, the Japanese encephalitis (JE) virus, the four serotypes of Dengue (Den) viruses, the tick-borne encephalitis (TBE) virus, and also the West Nile (WN) virus which recently has also appeared in North America as a pathogen in humans and in various bird species.

The genus pestiviruses contains animal pathogens of great economic importance, i.e. the classical porcine fever (CPF) virus, the bovine viral diarrhoea (BVD) virus and the border disease virus (BDV).

The genus hepaciviruses comprises the different subtypes of hepatitis C virus (HCV) and related viruses.

These three genera are combined in the family of Flaviviridae, since all representatives of this family have a nearly identical genome structure and show agreement in numerous structural and functional properties. All flaviviruses are relatively small, enveloped viruses which comprise a single-stranded RNA molecule with mRNA polarity as genome. The genome has a long open reading frame that codes for all proteins in the form of a polyprotein. The individual mature virus proteins are formed by the activity of viral and cellular proteases. The arrangement of the individual virus proteins in the genome is the same for all flaviviruses and starts at the 5' end with the capsid protein, the surface proteins and a series of non-structure proteins, the last of which is the viral polymerase. As a special feature, the pestiviruses furthermore contain an autoprotease in front of the capsid protein. The nucleocapsid of the flaviviruses is formed by just one single viral protein, i.e. the capsid protein, and surrounds the viral genome.

The exact three-dimensional structure of most of the capsid protein is known for West Nile Virus (Dokland et al., 2004; PDB acc. 1SFK) and Dengue virus (Ma et al., 2004; PDB acc. 1R6R) which superimpose very well. Additionally, amino acid sequences of further flaviviridae capsid proteins have numerous correlations, so that numerous structural similarities exist. The similarities in representatives of the same genus naturally will be even greater than between representatives of different genera. In all instances, the capsid protein is a rather small protein having a length of approximately 100 to 190 amino acids. It has an unusually high portion of basic amino acids, i.e. of the amino acids lysine and arginine. It is assumed that the basic amino acids are important for the interaction with the viral RNA (Khromykh and Westaway, 1996). Yet, all flavivirus capsid proteins also have characteristic hydrophobic sections. Such a hydrophobic section always is formed by the carboxy-terminal approximately 20 amino acids. This section serves as an internal signal sequence for the surface structure protein following in the genome sequence. By this signal sequence which during protein syntheses is integrated in the membrane of the endoplasmatic reticulum, the capsid protein initially is anchored in the membrane. Later on, the anchor is proteolytically cleaved. In addition, there are internal hydrophobic sections. In representatives of the genus flaviviruses, the functional importance of an internal hydrophobic domain has been described (Markoff et al. 1997). The authors have indicated the borders of this domain for a series of flaviviruses as follows: Dengue 1: 46-67, Dengue 2: 46-66, Dengue 3: 46-67, Dengue 4: 45-65, Japanese encephalitis: 46-62, West Nile: 46-62, Murray Valley encephalitis: 46-62, Saint Louis encephalitis: 45-61, yellow fever: 43-58, Langat: 42-54, Powassan: 40-52, TBE: 42-54. Also for hepatitis C virus, a functionally important internal hydrophobic domain has been identified (Hope and McLauchlan, 2000), extending from amino acids 119 to 145, in particular from 125 to 144. Also pestiviruses have short internal sections of mainly hydrophobic character.

Vaccines have been successfully used against some flaviviruses. Thus, there are live vaccines against the YF virus, the JE virus and the CPF virus, and inactivated vaccines are employed against JE and TBE. In view of the great importance of the flaviviruses in human and veterinary medicine, there is a high demand in the development of new and improved vaccines.

A series of attenuated flaviviruses is known whose attenuation is based on mutations in various regions of the genome. Attenuating mutations have been observed either in naturally occurring strains, obtained by serial passages of viruses in the laboratory, prepared by selection of mutants in the presence of neutralizing antibodies or by the targeted introduction of mutations with the assistance of recombinant cloning techniques. There exist infectious cDNA clones of several flaviviruses, and the skilled artisan knows how to prepare such clones. With the assistance of these infectious cDNA clones, according to the prior art, mutations can be specifically introduced into the genome of flaviviruses.

Known mutations for attenuating flaviviruses are found in the following sections of the genome:

Envelope proteins: Most of the observations of attenuating mutations relate to the envelope protein E (genus flavivirus) (reviewed in McMinn, 1997; new e.g. Mandl et al., 2000). Likewise, attenuating mutations in protein E(rns) (genus pestivirus) have been described (Meyers et al., 1999).

Non-structure proteins: A point mutation in protein NS1 of the Kunjin virus led to a delayed replication and, thus, attenuation (Hall et al., 1999). Attenuating mutations have also been described in the proteins NS3 (Butrapet et al., 2000) and NS5 (Xie et al., 1998).

Non-coding genomic section: Attenuation of the TBE virus by deletions in the 3'-terminal non-coding region has been described (Mandl et al., 1998). With Dengue viruses, experimental vaccines having deletions both in the 5' and in the 3' non-coding regions have been prepared (Lai et al., 1998). It is assumed that the molecular basis of the attenuation of these viruses is the adverse effect on the viral replication by these mutations.

The EP 1373478 B1 describes an attenuated flavivirus with deletions in the capsid protein.

An object of the present invention is to provide attenuated flaviviruses with a minimum site of mutations within the capsid protein, in particular only at one site of the viral capsid protein, which are capable of being passaged in cell culture and which are resistant to reverting to the virulent phenotype.

This goal is achieved by the subject matter of the claims. In particular, the invention provides a mutant virus of the family Flaviviridae, comprising a deletion in the capsid protein of at least 20 successive amino acids, without any further deletion, substitution or insertion mutation within the capsid protein except of amino acids adjacent to the deletion, which may be substituted. The inventive capsid protein thus only comprises one site of alteration, i.e. the relatively large deletion of at least 20 amino acids. The amino acids neighbouring to this deletion might be subject of an amino acid substitution mutation. This can be caused through the deletion on the nucleotide level encoding the capsid protein. One deletion of the nucleotide does not necessarily require the deletion of exactly the same nucleotide triplets that would encode the amino acid deletion. Shifts of one or two nucleotides on either end are possible, however the remaining sequence still has to be in frame. This means that a deletion might remove a nucleotide 5' of the deletion and at the same time one additional nucleotide remains next to the 3' end triplet adjacent to the deleted frame. In this case a new 5' triplet (not deleted) would remain with the first two nucleotides of the 5' triplet adjacent to the deletion and one nucleotide from the 3' end of the deletion (the last nucleotide encoding the last deleted amino acid). This can lead to a substitution mutation of the capsid amino acid sequence next to the deletion although on the nucleotide level only one deletion (even without any substitution) occurred. Of course further combinations are possible where the 5' (not deleted) triplet lacks two nucleotides and receives two originally from the 3' end of the deletion, or one or two nucleotides are removed at the 3' end of the deletion and are complemented by the 5' end of the deletion. Thus for the remaining nucleotide sequence no frame-shift occurs.

The present invention is applicable to all representatives of flaviviruses. Within the scope of this application, the term "flaviviruses" thus relates to all the representatives of the family Flaviviridae, except where it is expressly pointed out that only the representatives of the genus flavivirus is meant. Preferably the virus is a flavivirus (genus), pestivirus or hepacivirus, especially an arthropod borne virus, in more especially preferred embodiments a mosquito borne virus. Particularly preferred representatives of flaviviruses with which the present invention is realised are selected from the group consisting of yellow fever virus, the Japanese encephalitis virus, the four serotypes of Dengue viruses, tick-borne encephalitis virus, West Nile virus, Murray Valley encephalitis virus, Saint Louis encephalitis virus, Powassan virus, classical porcine fever virus, bovine viral diarrhoea virus, border disease virus, and hepatitis C virus. These representatives are particularly suitable for the present invention because of their known pathogenicity for humans and animals, since for these representatives the demand for a suitable attenuated live vaccine is particularly high. Specifically preferred viruses are West Nile Virus, Japanese encephalitis virus and Dengue viruses.

Although a series of attenuated flaviviruses has already been described in the prior art, and although EP 1373478 B1 describes deletions in the capsid protein as an advantageous attenuating principle for flaviviruses, it was surprising that flaviviruses which contain the large capsid protein deletion according to the present invention lead to a reliable attenuation of the flavivirus, can be effectively produced in cell culture, and can be employed as flavivirus live vaccines. Despite the substantial capsid protein mutation according to this invention, a propagation of the attenuated virus may take place in the vaccinated subject after administering the virus according to the invention as live vaccine. This results in a series of advantages over inactivated vaccines.

Especially surprising was the finding that flavivirus mutants according to the present invention are capable of being passaged in cell culture. The ability to efficiently passage a live vaccine in cell culture can represent a decisive advantage for the cost-effective production, amplification, and propagation of such a vaccine. Furthermore, the flavivirus mutants according to the present invention are also particularly advantageous with regard to safety and regulatory requirements, as they can be produced in approved cell lines and do not require animal propagation systems, which might constitute a safety hazard.

Moreover, the mutants according to the present invention are particularly resistant to reverting to the virulent phenotype and thus are excellently suited for a broad application in humans. In particular it was found that, although a deletion of at least 20 amino acids is large for the capsid protein of about 100 to 180 amino acids, stable viruses can be obtained which are capable of being passaged in cell culture and thus, can effectively be produced without the need of specific or fragile propagation regimes and/or without the introduction of further mutations at other loci within the capsid protein.

Thus, the present invention has significant advantages over the previously described forms of live vaccines:
- the longer deletion strongly increases safety since the danger of reversion to a wild-type sequence of a virulent phenotype is inversely correlated with the length of the deletion,
- introducing only a single deletion mutation without the need to select for additional mutations is a simpler and more straightforward approach to generate a flavivirus live vaccine, and
- the ability to passage the live vaccine in cell culture is advantageous for production of the vaccine and allows application as cell-culture grown virus particles.

The term "capable of being passaged in cell culture" is used herein to define the feature of the virus mutants to efficiently infect cell lines, and amplify and spread in cultures of these cells. Appropriate cell lines may be selected as described below. Supernatants from such cell cultures can be used to infect fresh cultured cells, i.e. these live vaccines can be passaged in cell culture.

The term "live vaccine" as used herein means that viral particles, components, or nucleic acids of the viral vaccine are capable of self-amplification and protein expression in vivo in the host. This definition of live vaccines includes infectious particles, single-round infectious virus-like particles and self-replicating nucleic acids (replicons). All of these preparations, as a common feature, will self-amplify in the host and produce viral components (nucleic acids and proteins) in vivo and thus are stimulating the innate and adaptive immune response similarly as in the course of wild-type virus infections. Furthermore, the subgroup of live vaccines which are capable of being passaged in cell culture (as defined above) are included. The definition of live vaccines excludes all non-replicating vaccines, i.e. inactivated vaccines, subunit vaccines (i.e. protein components of viruses prepared either by separation from infectious virus or by recombinant expression) and non-replicating nucleic acid vaccines consisting of DNA or RNA incapable of self-replication.

The terms "infectivity" or "infectious" are used herein to describe the ability of a viral particle or nucleic acid to initiate self-amplification in a suitable host cell. Thus "infectivity" or "infectious" describe a process rather than a property as it depends on properties both of the infectious agent or component, and of the host cell, as well as the mode of introduction of the agent/component into the host cell. For example, a viral particle may be infectious for some cells, but not for others. Some nucleic acids are infectious if appropriately transfected (e.g. by electroporation or gene gun bombardment) into cells in which they initiate cycles of self-replication, but may not be infectious upon inappropriate modes of inoculation. A subviral particle may be "single-round infectious", i.e. able to mediate entry of a self-replicating nucleic acid into a host cell only once.

"Attenuation" or "attenuated" as used herein means a reduction of viral virulence. Virulence is defined as the ability of a virus to cause disease in a particular host. Thus the term "attenuated" is synonymous to "less pathogenic" or sometimes to "apathogenic".

The term "viability" is used frequently in the context of viral live vaccines in the prior art. However, since viruses are not autonomous living organisms, but rather chemical structures which can be amplified by appropriate host cells, the term viability is not unambiguously defined and therefore avoided in the description of the present invention. In a more general sense, viral viability means the ability of a viral particle, component or nucleic acid for self-amplification in a host cell. For example, in EP 1373478 B1 the term viability is used in this broader sense. In said broader sense the term viability is synonymous to the definition of a live vaccine as defined herein. In a more restricted sense, viral viability may also mean "capable of being passaged in cell culture" as defined herein.

For the preparation of conventional inactivated vaccines it is necessary to produce large amounts of infectious and virulent virus. Also with recombinantly prepared inactivated vaccines, large amounts of antigen must be produced and purified. With a live virus, the amounts to be produced are substantially smaller, since viral proteins and nucleic acids are produced within the body of the vaccinated subject, whereby the production costs of live vaccines in general are substantially lower than those of inactivated vaccines. Moreover, not a virulent, but an apathogenic virus is produced, and therefore the production does not involve a health risk. Conventional inactivated flavivirus vaccines are prepared by inactivating infectious particles by a treatment with formalin, causing a certain change of the antigen structure. In the vaccinated subject, primarily a humoral immune response to structural proteins whose antigen structures do not exactly correspond to the native forms is induced, and not an immune response to non-structural proteins whose importance, however, is very high for the build-up of a long-lasting immunity and for the formation of cytotoxic T cells. Apart from the deletion, the virus of the invention does not contain a further mutation within the capsid protein and thus, the remaining not-modified viral proteins and not-modified portions are excellent cellular targets for the stimulation of the immune system.

The inventive attenuated flavivirus, particularly according to the preferred embodiments thereof, moreover has still further advantages over the conventional flaviviruses employed for vaccines and experimental live vaccines prepared by genetic engineering methods:

Currently used flavivirus live vaccines are normally passaged in the laboratory many times, which leads to a plurality of mutations whose meaning for the biology of these viruses in detail has not yet been completely understood and whose respective contribution to the attenuation of these viruses, as well as the interaction between the individual attenuated mutations are not yet completely known (for JE, cf. Nitayaphan et al., 1990; for YF, cf. Post et al., 1992; for CPF, cf. Bjorklund et al., 1998). Some mutations are also located in antigens which are particularly important for the immune response, such as surface protein E. Therefore, certain antigen determinants are present in an altered form as compared to the wild-type virus. The complexity of the genetic basis of the attenuation of these viruses does not allow the direct application of the principles forming the basis of the attenuation to other flaviviruses.

In contrast, in the mutated virus according to the present invention only defined and generally applicable attenuated mutations are introduced in the capsid protein, whereby it is not necessary to change a protein which is particularly important for the immune response (the envelope proteins or certain non-structural proteins, such as NS1 in the genus flavivirus). Preferred embodiments of the virus according to the invention thus do not comprise any further mutations, particularly not in the envelope proteins as well as in other proteins involved in the immune response.

As has also been already mentioned above, a series of genetically engineered attenuated flaviviruses has been described in which the attenuation is based on point mutations. For these it is relatively easy to revert genetically. Also the reversion of a virus, attenuated by point mutation, to a virulent phenotype by a second point mutation has been described (Mandl et al., 2000). In contrast, in the virus according to the invention, the attenuation is achieved by a deletion, the reversion of which to the wild-type is impossible.

In further described cases, the attenuation is based on changes in the envelope proteins important to the immune response, or in sections of the genome which are important for replication and translation. Neither a change in the antigen structure of envelope proteins, nor a substantial adverse effect on the replication or translation is desirable, if an immune response as natural and efficient as possible is to be elicited. These disadvantages are overcome by the present invention in which merely an inner structural component, yet not any envelope proteins, non-structural proteins or regulatory non-coding sections have been changed.

In a further set-up, the virus has been prepared by combining various viruses (chimeric viruses) (Guirakhoo et al., 2000). Since chimeric viruses are organisms in which genes of pathogenic viruses are newly combined with each other in a non-naturally occurring manner, the release of such viruses by vaccination harbours the risk of these chimeric viruses developing to new viruses the properties of which cannot be predicted. In contrast, the new virus does not constitute a combination of various virus genomes, and therefore it is not possible that a release by vaccination could cause the formation of a hitherto not naturally occurring virus species.

The introduction of the deletions of the invention into the capsid protein of flaviviruses, e.g., by aid of recombinant techniques, is possible for any skilled artisan by using methods known per se without undue experimental burden. The gene section coding for the respective capsid protein is known for all flaviviruses whose genomic sequence has been obtained to date, and for new flavivirus sequences it can be determined easily by sequence comparison. Of course, the deletions in this case must not lead to any shifting of the reading frame so that the carboxy-terminal hydrophobic region would be affected by the deletion. It is essential for this carboxy-terminal hydrophobic region to be largely maintained, and thus not to be affected by the deletion. With the techniques mentioned it is possible to propagate mutant, infectious viruses with all viral proteins, except for the capsid protein, being formed in native form. Replication and translation of these viruses then will not, or not essentially, be restricted. By propagation in cell cultures, preparations can be produced from these viruses which can be used as vaccine. In contrast to the unchanged wild-type virus, the viruses according to the invention, after having been inoculated into an appropriate host organism, exhibit an attenuated phenotype, i.e. they do not cause disease. Yet they induce the formation of a specific immune response. A host organism immunized with the inventive flavivirus live vaccine will be protected from a subsequent infection with the virulent wild-type, i.e. in contrast to the unprotected organism, a disease caused by the wild-type virus will not occur.

The inventive deletion in the region of the capsid protein will be particularly well suited for preparing a virus mutant suitable as a live vaccine if attention is paid to a number of characteristics by aid of which the properties of the vaccine can be improved in the preparation of a mutant suitable as a vaccine. The deletion to be provided according to the invention is larger than 20 amino acids so as to prepare suitable attenuated immunogenic viruses without the risk of reversion to the virulent virus type.

The deletion of the inventive flavivirus capsid protein may also comprise larger deletions, in particular of at least 21, preferably at least 22, 23, 24, 25, 26, 27, 28, 29, 30, 31, 32, 33, 34, 35, 36, or at least 37 successive amino acids. In special embodiments the upper limit is 48 deleted amino acids, to allow an efficient propagation in cell culture and therefore enabling stable production and less modified viral capsids. Thus the invention relates to a flavivirus capsid protein with a deletion of up to 47, preferably up to, 46, 45, 44, 43, 42, 41, 40, 39, 38, 37 or up to 36, amino acids.

Preferably, the deletions may reach as far as to 20 amino acids to the amino terminus and/or as far as to immediately in front of the beginning of the carboxy-terminal signal sequence.

In particular, the virus is capable of being passaged in cell culture and stable, preferably after at least 2 passages. Stability as used herein refers to genetic stability, in particular of the capsid protein. Viruses are selected for not expressing additional mutations, apart from the deletion as defined herein. The virus can be genetically stable after at least 1, 2, 3, 4, 5, 6, 7, 8, 9 or at least 10 passages.

A single viral capsid molecule of flaviviruses comprises 4 alpha helices, forming a three layered structure with alpha helix 1 in one layer, helix 2 in a middle layer and helix 4 in the third layer. Alpha helix 3 serves as a spacer. This capsid forms dimers which in turn again dimerize to tetramers. For this assembly the helices 1 and 4 are of greater importance than helix 2 and in particular helix 3. Therefore, the deletion preferably occurs in these intermediary helices 2 and 3. In an embodiment, the entire helices alpha 2 and alpha 3 are deleted. The N-terminus of helix 4 may also be affected by the deletion. In a preferred embodiment of the present invention, a C-terminal part of helix alpha 2, the entire helix alpha 3, and an N-terminal part of helix alpha 4 are deleted. The remainders of helices alpha 2 and 4 may form a fusion helix and thereby forming two layers instead of three. Thus, in special embodiments the deletion comprises at least one amino acid of alpha helix 2 of the wild type virus capsid protein, preferably at least a third of the amino acids of helix 2, more preferred at least half of the amino acids of helix 2. In an embodiment, the deletion comprises the C-terminal amino acids of helix 2. In further embodiments the deletion comprises at least one amino acid of alpha helix 3 of the wild type virus capsid protein, preferably at least one third of the amino acids of helix 3, more preferred at least two thirds of the amino acids of helix 3, most preferred the entire helix 3. In special embodiments the deletion comprises at least one amino acid of alpha helix 4 of the wild type virus capsid protein, preferably at least one third of the amino acids of helix 4, more preferred more preferred at least half of the amino acids of helix 4. In an embodiment, the deletion comprises the N-terminal amino acids of helix 4. Preferably helix 1 is unaffected by the deletion, and/or at least one third, preferably at least two thirds or three quarters of the amino acids of helix 4 are unaffected by the deletion.

In preferred embodiments the carboxy-terminal hydrophobic region of the capsid protein is not affected by the deletion—the deletions according to the invention do not involve the carboxy-terminal hydrophobic region of the capsid protein. It is known that this sequence is necessary for the correct formation of the envelope protein, encoded adjacently on the genome, and that it is removed from the mature capsid protein by proteolytic cleavage. The length of this signal sequence varies between individual flaviviruses, yet it can easily be determined by establishing hydrophilicity profiles (cf. FIG. 1). Accordingly, in preferred embodiments the deletion according to the invention does not involve this carboxy-terminal region.

The carboxy-terminal hydrophobic region relates at least to all the amino acids in this region which have a hydrophilicity score according to FIG. 1 of −1 and less. Particularly preferably, the C-terminal region having a hydrophilicity of below 0, according to FIG. 1, remains unchanged.

Preferred deletions according to the invention concern regions of internal hydrophobic domains. From FIG. 1 it can be seen that the capsid sequences of all flaviviruses, in addition to the above-indicated hydrophobic signal sequence at the carboxy terminus, furthermore contain sections of predominantly hydrophobic character in the midst of otherwise predominantly hydrophilic amino acid chains. Deletions by which regions of these internal domains are partially or completely removed will give rise to particularly suitable attenuated flavivirus live vaccines. As "internal hydrophobic domain" at least all those regions can be considered which have a negative hydrophilicity score in FIG. 1.

Figure 2:
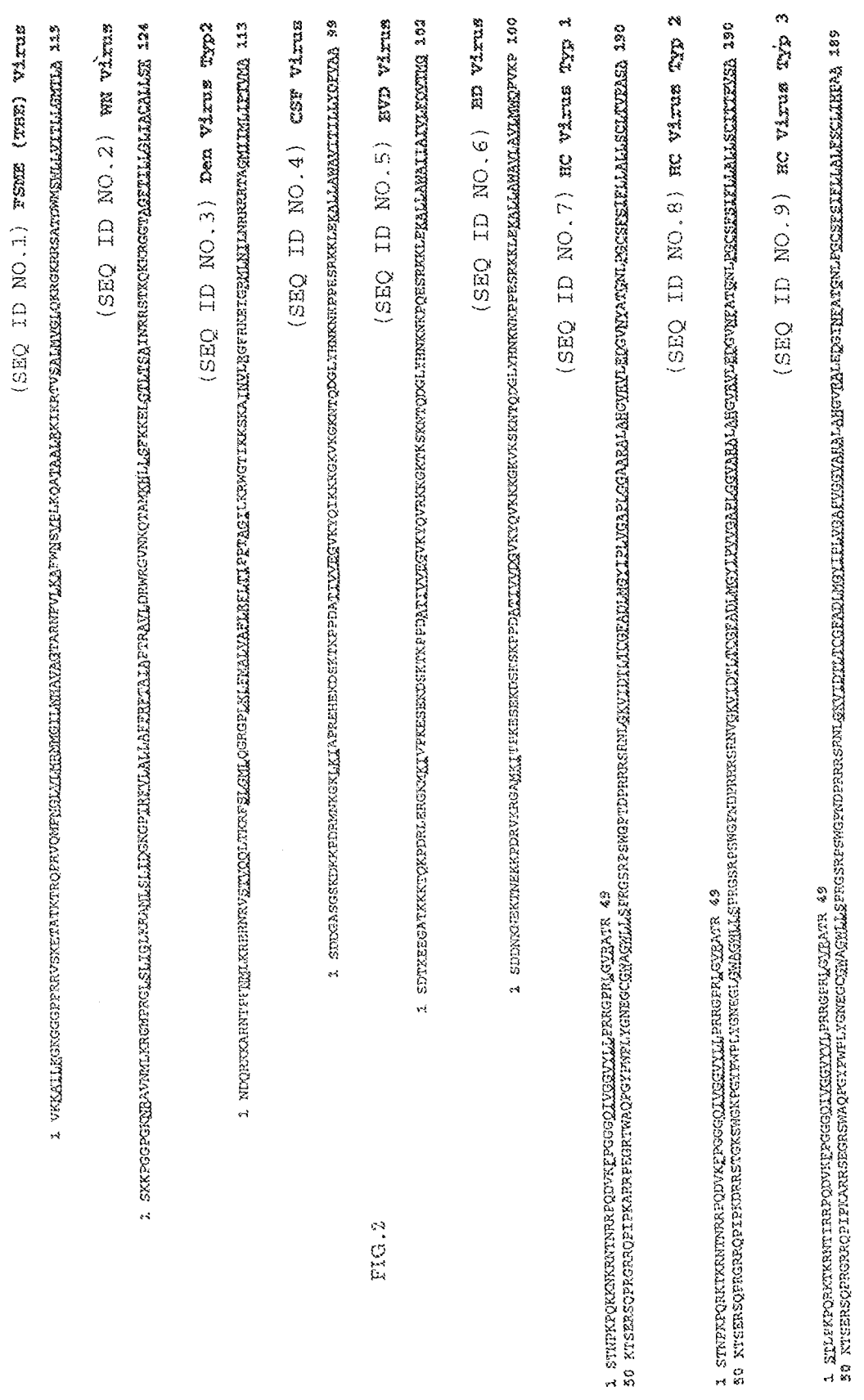

In FIG. 2, particularly preferred hydrophobic regions which may be at least partially deleted in a virus according to the invention are characterised for a number of flaviviruses. These regions can be determined by calculating the hydrophobicity profiles of the respective amino acid sequences. The regions underlined in FIG. 2 have been calculated with the algorithm of Kyte and Doolittle (1982) with a window size of 5. Alternatively, hydrophobic regions can also be calculated with window sizes of between 5 and 13 amino acid residues, or by other algorithms, such as those of Hopp and Woods (1981), wherein usually window sizes of between 3 and 11 can be chosen.

The hydrophilicity blots according to FIG. 1 have been calculated according to the algorithms of Kyte and Doolittle (1982) with a window size of 9 amino acid residues, or of Hopp and Woods (1981), respectively, with a window size of 7 amino acid residues. Preferred hydrophobic regions are chosen from Dengue 1: 46-67, Dengue 2: 46-66, Dengue 3: 46-67, Dengue 4: 45-65, Japanese encephalitis: 46-62, West Nile: 46-62, Murray Valley encephalitis: 46-62, Saint Louis encephalitis: 45-61, yellow fever: 43-58, Langat: 42-54, Powassan: 40-52, TBE: 42-54, and HCV: 119-145, in particular 125-144.

The allowable substitution mutation adjacent to the deletion is preferably selected from point mutations by which the hydrophobicity of the capsid protein is increased. Particularly preferred point mutations comprise the swapping of charged, or hydrophilic amino acids, respectively (such as, e.g., aspartic acid, glutamic acid, lysine, arginine, histidine, tryptophane, glutamine, asparagine, tyrosine, serine, etc.) to less polar amino acids or non-polar amino acids (such as, e.g., isoleucine, leucine, phenylalanine, methionine, alanine, valine etc.).

The deletion mutations in the capsid protein C according to the present invention can be combined with mutations elsewhere (outside the gene coding for capsid protein C) in the flavivirus genome, e.g. to further modulate the attenuated phenotype of the live vaccine.

In further aspects the present invention also relates to a a pharmaceutical composition, preferably a vaccine, comprising a virus as defined above. The pharmaceutical composition, in particular with live flaviviruses can be used as live vaccine for immunisation purposes.

In the composition according to the invention only a slight amount of virus is necessary for an efficient immunisation so that, per administration, $10^1$ to $10^7$, preferably $10^2$ to $10^6$, in particular $10^3$ to $10^5$, infectious units of flaviviruses are sufficient with the composition according to the invention. Preferably, the vaccine can be administered as a single dose with this amount of infectious units.

Preferably, the composition according to the invention further comprises active substances or auxiliary substances. Particularly preferred is the addition of antibiotics, such as neomycin or kanamycin, preservatives, such as thiomersal, and stabilizers, such as human albumin, lactose-sorbit, sorbit-gelatine, polygeline or salts, such as $MgCl_2$ or $MgSO_4$. In general, preferably amino acids, polysaccharides and (buffer) salts may be used as the additives.

In the preparation of the live vaccine according to the invention, it is recommendable—if it is to be administered to humans—to use non-transformed host cells, since in this manner both, the risk of a change of properties (e.g. an easy introduction of new, undesired mutations), and the risk of contaminations with components of these cells is avoided.

The invention also relates to a nucleic acid encoding the capsid protein of the mutated virus according to the present invention, preferably isolated or purified. Preferably, said nucleic acid molecule self-replicates in the host and may comprise all further nucleic acids of the flavivirus genome necessary for the RNA replication and virion formation in addition to the nucleic acid sequence encoding the capsid protein. As mentioned above the nucleic acid encoding the capsid protein may only comprise one deletion compared to a wild type virus nucleic acid which can also lead to substitution adjacent to the deletion. Next to the adjacent amino acids, or the encoding triplets thereof no frame shift occurs. Similarly the present invention also provides the capsid protein of the mutated virus itself, preferably in isolated or purified form. These nucleic acids or proteins may also be provided in form of a pharmaceutical composition, preferably a vaccine.

Such a nucleic acid or protein preparation, in particular in form of a vaccine, may also contain aminoglycoside antibiotics, such as neomycin or kanamycin, as is recommended by the FDA for plasmid vaccines, in addition to the nucleic acid. In the prior art, a whole series of the most varying strategies has been described for vaccination with "naked" nucleic acids (cf. e.g. WO 90/11092, WO 94/29469, WO 97/47197, incorporated herein by reference, liposome-mediated nucleic acid transfer, preferably nucleic acid transfer with (preferably biodegradable) microspheres, ...) or combination or mixtures thereof.

The live virus composition as well as the nucleic acid or capsid subunit composition may be prepared and/or used for the treatment or prevention of a flaviviridae infection. "Prevention" should not be understood in an absolute sense, i.e. that the occurrence of any further flavivirus infections are prohibited, but in the sense of a prophylactic use to reduce the risk of a flavivirus infection. The composition will result in an in vivo stimulation of the immune system and immunisation.

Finally, the present invention also relates to a method of producing a modified virus of the invention, characterized by the following steps:
providing a flavivirus or a flavivirus nucleic acid, wherein the flavivirus or the flavivirus nucleic acid encodes a capsid protein with a deletion as defined above,
propagating the flavivirus or the flavivirus nucleic acid in suitable host cells, and
recovering the virus particles propagated by the host cells.

The invention also relates to a method of producing a modified nucleic acid according to the invention, characterized by the following steps:
providing a flavivirus nucleic acid which encodes a capsid protein with a deletion as defined above,
inserting the nucleic acid into a suitable vector,
transforming suitable host cells with the vector,
amplifying the nucleic acid in said host cells,
recovering the nucleic acid from the host cells.

The flavivirus nucleic acid which encodes a capsid protein with a deletion as defined above may be DNA or RNA and may be provided by using appropriate reverse genetic systems or nucleic acid synthesis systems known in the art. A suitable host cell is e.g. E. coli. The nucleic acid recovered from the host cells may be transcribed into RNA.

Furthermore the nucleic acid or the capsid protein may be further isolated or purified and formulated in a pharmaceutical composition, preferably a vaccine.

Preferred host cells are selected from chicken embryo cells, primary chicken embryo cells, human diploid cell lines (e.g. WI-38, MRC-5), Vero cells, CHO cells, HEK293 cells, PER.C6® cells, primary hamster kidney cells, primary canine kidney cells or diploid fetal rhesus lung cells. Most preferred are Vero cells, especially ATCC CCL-81, and BHK-21 cells.

Host cell lines for the production of the vaccines can be selected based on the susceptibility of these cells for infection with wild-type virus strains. Since the infection process of wild-type and vaccine strains (in the cases of vaccines according to the present invention) is supposed to be identical, host cells to produce the vaccine can be selected from cells known by those skilled in the art to produce high quantity of the corresponding wild-type virus or this property can easily be evaluated by generally known virological techniques such as growth curve analyses, determination of viral titers and quantification of viral protein release.

The invention will be explained in more detail by way of the following Examples as well as by the drawing figures to which, however, it shall not be restricted.

FIGURES

Figure 1B:
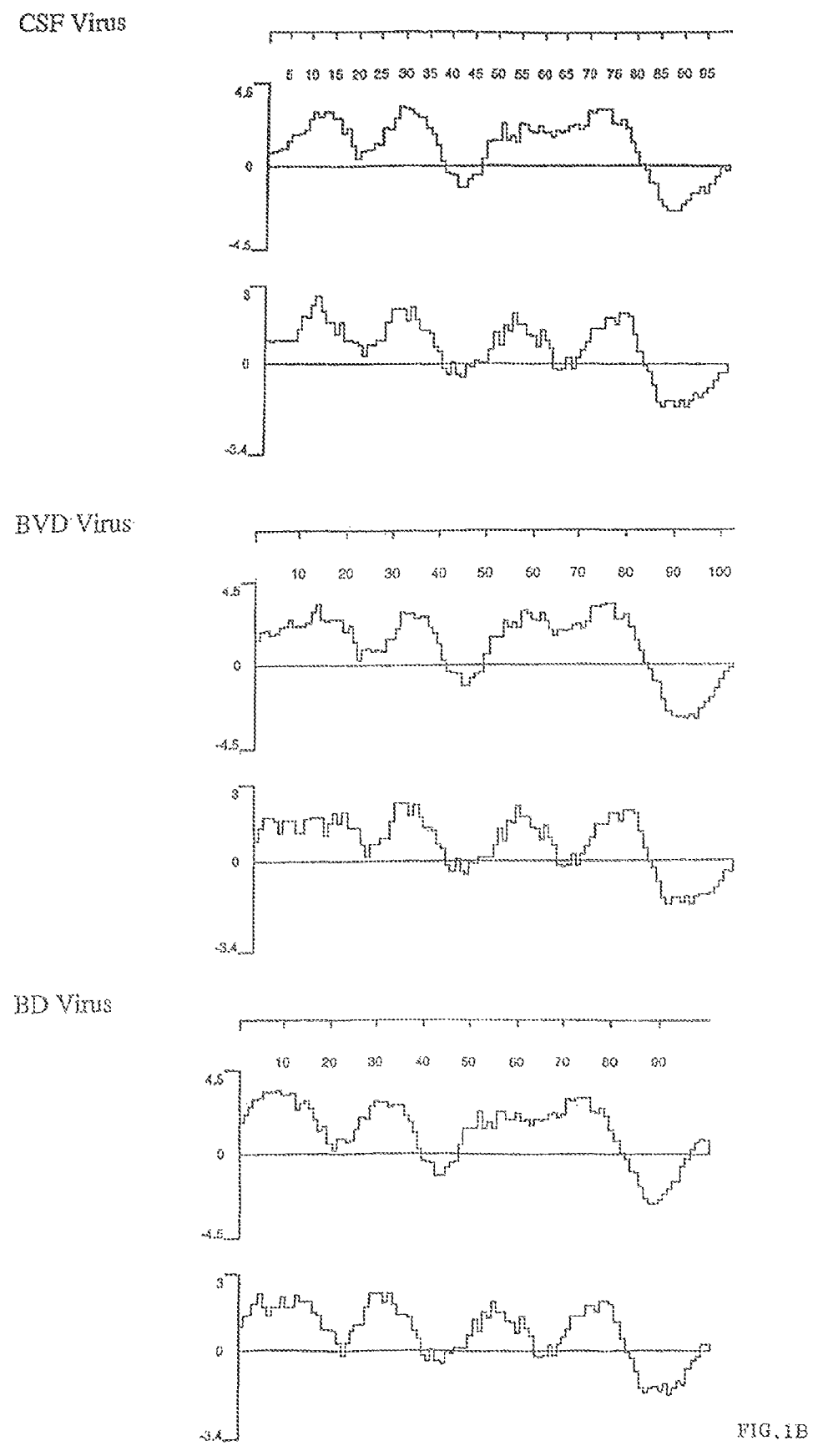

FIGS. 1A-C show hydrophilicity profiles of the capsid proteins of 3 representatives each of the 3 genera of the family Flaviviridae. Negative values indicate regions with predominantly hydrophobic character. The carboxy-terminal hydrophobic region is the signal sequence for the envelope protein following in the genome. For each protein, the hydrophilicity has been calculated and illustrated by way of example once according to the algorithm of Kyte and Doolittle (1982) with a window size of 9 amino acid residues (top) and once according to the algorithm of Hopp and Woods (1981) with a window size of 7 amino acid residues (bottom).

FIG. 2 shows the sequence alignment of the capsid proteins of 3 representatives each of the 3 genera of the family Flaviviridae. Sequence sections having predominantly hydrophobic character (determined according to Kyte and Doolittle with a window size of 5) have been underlined. In this instance, the respective most carboxy-terminally arranged section represents the signal sequence for the subsequent envelope protein. In this section there must not be any deletions. The other (internal) hydrophobic sections represent preferred regions for attenuating deletions. In contrast to the following Figures, the sequence is shown without M at position 1.

FIG. 3 shows the characterization of mutants CD36 and CD37 (A to F). Approximately $10^6$ Vero cells were infected at an MOI of 1 with the indicated virus preparation. Wild-type virus and infection media were used as the respective positive and negative controls. (A) RNA replication was measured by real time PCR at the indicated time points. (B) The RNA export kinetics of mutants CD36 and CD37 was monitored by real time PCR. (C) The percentage of exported to total RNA (intra-plus extracellular RNA) was calculated for the 48 h time point. (D) Release of viral particles into the supernatant was assessed by hemagglutination assay. (E) Cytotoxicity was assessed by CytoTox 96 Non-Radioactive Cytotoxicity Assay (Promega) using supernatants of the same samples. The respective $OD_{490}$ values, representing LDH release of disintegrating cells, are shown on the left. (F) shows the specific infectivity of WNV capsid deletion mutants CD37 and CD36. The specific infectivity of second site mutants was calculated by determining the ratio of RNA (real time PCR) to infectious units (focus assay) in virus stock preparations (Table 1). Logarithmic means of two independent experiments are shown; the error bars indicate standard deviations. FFU (focus forming units).

FIG. 4 shows secondary structure predictions for sequences of wild-type (A), deletion mutations CD10 and CD36 (B), and deletion mutations CD7/3 and CD37 (C). In (A), the secondary structure prediction and the hydrophobicity blot are shown for the WNV V76/1 sequence. Exclusively residues R23 to R98, which are also present in the Kunjin protein C crystal structure, are shown. In (B) and (C), the deletions are illustrated both on the wild-type and mutant sequences (open box). Furthermore, the resulting truncated sequences are shown (bottom panels), as are the corresponding hydrophobicity plots (below each mutant). All secondary structure predictions were performed using PsiPred, the hydrophobicity blots were generated according to the algorithm of Kyte and Doolittle. Wt, wild-type.

FIG. 5 (A) shows the secondary structure prediction for the Kunjin subtype of WNV in comparison to the crystal structure (Dokland, T. et al., 2004). The secondary structure prediction was performed using PsiPred (Jones, D. T., 1999); only residues R23 to R98, which are also present in the crystal structure, were analyzed. The secondary structure prediction (Pred) is shown in the middle with the confidence values listed on top (Conf; 9 high, 0 low). The corresponding amino acid sequence (AA) is listed below; furthermore, within the amino acid sequence, the residues involved in helix formation within the crystal structure are highlighted in italics and bold. The four helices are designated as in the crystal structure, i.e. alpha-1 to alpha-4. (B) shows the secondary structure predictions for the WNV isolate used in the present invention, i.e. WNV NY99. In contrast to (A), the amino acid sequence starts with the initiator M and includes also the C-terminal signal sequence (G105-A123, underlined). (C-F) show the secondary structure predictions for capsid deletion mutants CD7/3, CD37, CD10 and CD36. For clarity, the amino acids fused subsequent to the deletions are highlighted in bold; furthermore, in contrast to the wild-type sequences (A and B), only the numbers of the fused residues are shown. (G-H) show the secondary structure predictions for mutant CD48 and CD48 duplication, respectively; CD48 duplication originated from CD48 by duplication of residues M16-E39/L88-A94. The respective residues are highlighted in dark and light grey, respectively. Furthermore, residues predicted to form coiled coils are underlined and residues fused by either deletions or duplications are highlighted in bold. H, helix; C, coil; E, extended (beta-strand/sheet).

FIG. 6 (A) shows the alignment of the capsid protein sequences of WNV NY99 and WNV, subtype Kunjin. The analysis was performed by using BLAST (Altschul, S. F. et al., 1997) and restricted to residues which are also present in the crystal structure (Dokland, T. et al., 2004). (B) shows the alignment of the capsid protein sequences of WNV NY99 and Dengue virus 2 capsid protein; the analysis was performed as described in (A) and restricted to residues N15 to R98. Numbering is according to the sequence of WNV NY99. Cons., consensus sequence.

Figure 7:
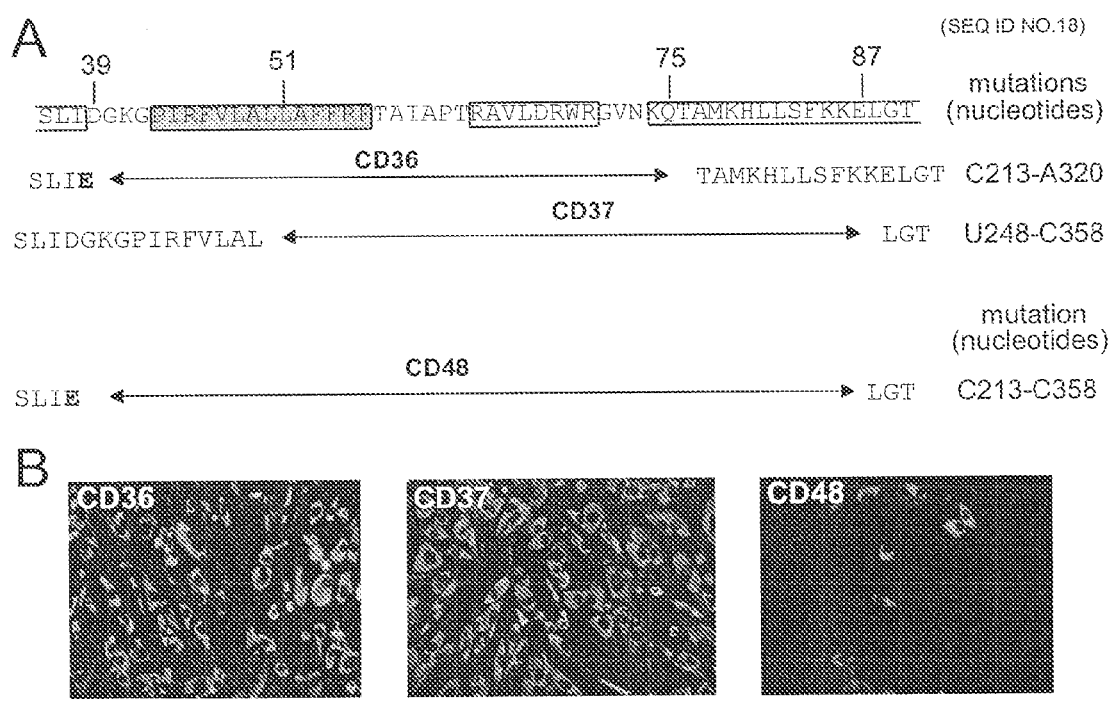

FIG. 7 shows mutations in the WNV capsid protein. (A) Large deletions CD36 and CD37, identified subsequent to passaging of mutants CD10 and CD7/3, respectively. The helical parts of the capsid protein are indicated by boxes and helix α2 is highlighted in grey. The positions of the large deletions are indicated by arrows. Furthermore, an artificial large deletion mutant (i.e. CD48) was constructed, lacking all residues which had been spontaneously deleted in both CD36 and CD37. The precise nucleotide deletions are shown on the right. (B) Immunofluorescence analysis of large deletions mutants. The large deletions (i.e. CD36, CD37 and CD48) were engineered into the infectious cDNA clone and mutants were tested by transfecting BHK-21 cells with wild-type or mutant in vitro transcribed RNAs as indicated. CD36 (left), CD37 (middle), CD48 (right). As a control, mock transfected cells were used. 48 h posttransfection, intracellular protein E expression was visualized by immunofluorescence staining using a polyclonal antibody directed against JEV protein E which is cross-reactive to WNV protein E. As secondary antibody, an anti-rabbit FITC-conjugate was used.

EXAMPLES

Example 1

Construction of Impaired WNV Capsid Deletion Mutants and Selection of Mutants with Large Deletions, which are Capable of being Passaged in Cell Culture Experimental Procedures Cells and virus. Vero (ATCC CCL-81) cells were grown in Eagle's minimal essential medium (EMEM, Cambrex) supplemented with 10% fetal bovine serum (FBS, PAA), 1.5% glutamine (200 mM, Cambrex), and 1% penicillin/streptomycin (10,000 U/ml penicillin, 10 mg/ml streptomycin, Sigma). Infections were performed in the presence of 2% instead of 10% FBS. BHK-21 cells used for introduction of in vitro transcribed RNA were handled in growth medium (EMEM supplemented with 5% FBS, 1% glutamine, 0.5% neomycin (10 mg/ml, Sigma)) and maintenance medium (EMEM supplemented with 1% FBS, 1% glutamine, 0.5% neomycin and 15 mM HEPES, pH 7.4) as described in Kofler, R. M. et al. (2002).

The WNV strain used in this study was originally isolated from a dead crow collected in New York City in 1999 (WNV NY99, kindly provided by Ernest Gould and Bob Shope). After its isolation, the virus was passaged three times in Vero cells prior to the construction of the infectious cDNA clone.

Construction of WNV cDNA clones. The WNV RNA was isolated as described by Mandl, C. W. et al. (1997). The synthesis of WNV cDNA was performed by taking advantage of the cDNA synthesis kit of Roche Applied Science and sequence specific primers appropriate for covering the entire WNV genome. These cDNAs were used for the amplification of DNA fragments by PCR using primers containing PacI and NotI restriction sites. In addition to the restriction sites, the primers for the amplification of the very 5'-end and the very 3'-end contained a T7 transcription promoter sequence (Mandl, C. W. et al., 1997) and a sequence encoding the hepatitis delta virus ribozyme (Varnayski, A. N. et al., 2000), respectively. All PCR fragments were cloned into pBR322 (Bolivar, F. et al., 1977) which had been modified by replacing the BspEI-AatII fragment encoding the tetracycline resistance gene with a multiple cloning site (BspEI-SwaI-PacI-NotI-SwaI-AatII).

Subsequent to final assembly steps, two plasmids were obtained, i.e. WNV-K1 comprising the T7 transcription promoter and the cDNA of the 5' one-third of the WNV genome (bp 1 to 3339) and WNV-K4 containing the 3' two-thirds of the WNV genome (bp 3282 to 11029) followed by the hepatitis delta virus ribozyme. As a unique BstEII site (3321/3326) is present in both plasmids, full-length DNA templates for in vitro transcription were generated by enzymatic digest with BstEII and ligation of the two plasmids in vitro.

All constructs were amplified in E. coli DH5alpha cells and characterized by complete sequencing of both strands of the entire inserts.

Construction of WNV capsid deletion mutants. For the introduction of deletions into the capsid protein within plasmid WNV-K1, the Gene Tailor site-directed mutagenesis system (Invitrogen) was used. Accordingly, mutants CD7/3 and CD10 were constructed, lacking amino acids F53-159 and 144-F53, respectively.

In vitro RNA transcription and transfection. In vitro transcription with T7 RNA polymerase (Ambion T7 Megascript transcription kit) and transfection of BHK-21 cells by electroporation was performed as described in previous studies (Elshuber, S. et al., 2003; Kofler, R. M. et al., 2002). In the case of transcription reactions required as standards in real-time PCR analysis, the template DNA, which had been generated by digestion of WNV-K1 with BstEII, was degraded by incubation with DNaseI for 15 min at 37° C., and the RNA was purified and separated from unincorporated nucleotides by using an RNeasy Mini kit (QIAGEN). RNA concentrations were estimated from band intensities or, for determination of the RNA standard concentration, measured spectrophotometrically.

Immunofluorescence staining. Intracellular expression of WNV specific proteins was determined by indirect immunofluorescence (IF) staining of the envelope protein. Accordingly, RNA-transfected cells were seeded into 24-well plates and supplied with growth medium which was exchanged for maintenance medium at 20 h post transfection. After 24 or 48 h, cells were treated with 1:1 acetone/methanol for fixation and permeabilization. To specifically detect WNV E protein, a cross-reactive polyclonal antibody directed against Japanese encephalitis virus envelope protein was used (dilution 1:50). Staining was performed with a secondary fluorescein-isothiocyanate-conjugated anti-rabbit antibody (Jackson Immuno Research Laboratories) as suggested by the manufacturer.

Haemagglutination assay. For the detection of WNV viral and/or subviral particles in supernatants of infected cells, a rapid assay based on the agglutination of erythrocytes, which is induced by the interaction with viral envelope proteins, was applied (Guirakhoo, F. et al., 1989; Clarke, D. H and Casals, J., 1958). Briefly, virus supernatants were diluted 1:1 in borate-buffered saline (120 mM sodium chloride, 50 mM sodium borate, pH 9.0) containing 0.4% of bovine serum albumin for particle stabilization. Subsequently, this mixture was further diluted to produce a geometrical dilution row. 50 μl of each of the diluted samples were mixed with the same amount of a 0.5% solution of goose erythrocytes in round-bottomed 96-well plates and incubated for 3 h at room temperature. Virus-induced agglutination of erythrocytes was visible by the lack of sedimented erythrocytes; the examination of plates was performed by visual inspection.

Mutant stability. To assay the genetic stability of transfected mutants, supernatants of transfected cells were diluted until the end point of infectivity was reached. The supernatant corresponding to the end point was then transferred onto fresh cells and these passages were repeated at least twice. Subsequently, RNA was isolated and sequence analysis was performed by using the cDNA synthesis system of Roche Applied Science and standard PCR and sequencing protocols.

Production of virus stocks. For virus stock production, Vero cells were grown in growth medium as described above. Infection was performed with supernatants of cells derived from transfection of BHK-21 cells with in vitro transcribed mutant or wild-type RNA. Subsequently, infected Vero cells were maintained in growth medium in which the FBS has been replaced with 1% bovine serum albumin and 15 mM HEPES, pH 7.4. Subsequent to the onset of CPE, supernatants were cleared from cell debris by low speed centrifugation (30 min at 4° C., 10,000 rpm in Avanti JA-12 rotor) and stored in aliquots at −80° C.

Results

Reconstitution of infectious WNV from two partial cDNA clones. For the generation of WNV capsid deletion mutants, it was first necessary to construct an infectious WNV cDNA clone. Thus, the genome of WNV was cloned as two partial cDNAs into plasmid pBR322 as described in the experimental procedures section. Accordingly, two plasmids were generated, WNV-K1 and WNV-K4 containing the 5'-one-third and the 3'-two-thirds of the WNV genome, respectively. To generate full-length infectious RNA, plasmids WNV-K1 and WNV-K4 were ligated in vitro and the ligation product served as template for in vitro transcription. Subsequently, the full-length genomic RNA was used to transfect BHK-21 cells. To test for virus replication and expression of proteins, the transfected cells were examined by immunofluorescence. At 24 h post electroporation, the number of positive cells did not exceed 10% of cells; this is a typical result when in vitro ligated DNA templates are used. However, at 48 h post electroporation, 100% of cells gave a positive result in immunofluorescence indicating that virus capable of infecting surrounding, non-transfected cells was produced. The infectivity of wild-type virus was verified by transfer of supernatants onto fresh BHK-21 or Vero cells and subsequent testing by immunofluorescence and hemagglutination assay. Thus, the infectious WNV cDNA clone was successfully constructed.

Construction and testing of WNV capsid deletion mutants. In order to generate a live-attenuated vaccine candidate directed against WNV, deletions were introduced into the region encoding the WNV capsid protein. The technology was successfully used previously to elicit highly protective immune responses with a tick-borne encephalitis virus vaccine in an experimental animal model (Kofler, R. M. et al., 2002; Kofler, R. M. et al., 2003). For that purpose, deletions of 7 (F53-159) and 10 (144-F53) amino acids were introduced into the region encoding the capsid protein, which resides in plasmid WNV-K1 containing the 5'-one-third of the WNV genome. Both deletions affected helix alpha 2 which partially overlaps with a central hydrophobic sequence (Markoff, L. 1997; Ma, L. et al., 2004). The resulting mutants, named CD7/3 and CD10, were tested for their capability to replicate and to express proteins as described in the previous section. Intracellular expression of envelope protein was determined at 24 h post electroporation, using wild-type RNA transfected and untransfected cells as positive and negative controls, respectively. As expected, the two mutants as well as the wild-type control were capable of replicating and expressing envelope protein, as indicated by positive immunofluorescence results for approximately 10% of cells.

The capability of the WNV capsid deletion mutants to infect surrounding, untransfected cells was assessed by immunofluorescence staining at 48 h post electroporation. As mentioned above, an increase in the number of positive cells from 24 h to 48 h post electroporation is indicative for the infectivity of the transfected viral genomes. Indeed, for the wild-type control, 100% of cells stained positive at 48 h post electroporation. In contrast, infectivity was significantly reduced for mutants CD7/3 and CD10; the latter mutant was almost incapable of producing infectious virus progeny.

To further evaluate whether or not supernatants contained infectious material and, furthermore, to determine the export of viral antigen by the infected cells, a monolayer of Vero cells was infected with supernatants harvested at 48 h post electroporation. Envelope protein content in supernatants was analysed by haemagglutination assay at day 6 post infection. Export of envelope protein and thus also infectivity was detectable for all mutants. However, mutants CD7/3 and CD10 exported significantly less particles than wild-type; the titers determined by haemagglutination assay revealed a 2-fold and 10-fold reduction for mutants CD7/3 and CD10, respectively.

To summarize, mutants CD7/3 and CD10 differ from wild-type with respect to the production of infectious particles; both immunofluorescence and haemagglutination assay indicated that the infectivity of mutants is impaired.

Selection of large deletion mutants by performing multiple end point passages. To select for mutants with improved cell culture growth properties, mutants CD7/3 and CD10 were passaged three times in Vero cells; throughout these experiments, supernatants titrated to the end point of infectivity were used. Interestingly, the capability of the mutants to grow in cell culture was improved as determined by hemagglutination assay. To investigate if these changes in phenotype were a direct result of additional alterations within the capsid protein sequence, viral RNA was isolated from supernatants of infected cells and subject to RT-PCR and sequence analysis. Notably, sequencing of the region encoding the capsid protein indeed verified the appearance of such mutations. Surprisingly, mutations in which the original deletion was even enlarged were identified. Thus, passaging of deletion mutants CD7/3 and CD10 resulted in the appearance of a deletion of 37 amino acids and 36 amino acids (CD37 and CD36), respectively. The exact position of the deletions is listed in Table 1. It is worth noting that no additional mutation was identified when the entire genome was analyzed.

Subsequently, virus stocks were produced as described in the experimental procedures section. Notably, for the original mutants, the production of virus stocks was not possible, as second site mutations rapidly emerged. In contrast, both the CD37 and the CD36 mutant enabled the production of virus stocks with titers >$10^7$ FFU/ml, without the necessity of performing mouse brain passages. The two virus stock preparations were subject to three end point passages and sequence analysis was performed to ensure that they remained stable and no further mutations emerged. Thus, the genetic stability was confirmed for both mutants (Table 1).

To summarize, by performing multiple passages in Vero cells, large capsid deletion mutants without mutations elsewhere in the capsid protein were identified which could readily be passaged in cell culture when compared to original mutants comprising 7 and 10 amino acids only. Furthermore, both the CD37 and the CD36 mutants were, in contrast to the CD7/3 and CD10 deletions, genetically stable and enabled the production of high titer virus stocks. The finding that enlarging a deletion is improving cell culture growth properties was indeed surprising. Immunofluorescence staining at 48 h post transfection of in vitro transcribed RNA (FIG. 7B) suggested that mutants CD36 and CD37 were indeed viable. Finally, it is important to note that there is no potential of such large deletions to revert to wild-type.

Example 2

Characterization of Deletion Mutants CD37 and CD36 in Cell Culture

Experimental Procedures

RNA replication and export. Intracellular RNA replication was monitored by real-time PCR as described previously (Kofler, R. M. et al., 2006; Orlinger, K. K. et al., 2006) with minor modifications. Briefly, Vero cells grown in 6-well plates were incubated with WNV wild-type and mutant virus stock preparations at a multiplicity of infection (MOI) of 1.0. After 1 h, the cell monolayer was washed and supplied with growth medium which contained 1% BSA and 15 mM HEPES instead of FBS. At selected time points, cells were detached by trypsin incubation and washed twice in phosphate-buffered saline (PBS; pH 7.4) containing 1% BSA. Cytoplasmic RNA was purified from these cells (RNeasy mini kit, Qiagen) and was subject to real-time PCR (PE Applied Biosystems) quantification according to previous studies (Kofler, R. M. et al., 2006; Orlinger, K. K. et al., 2006). The respective primers (5"-TCAGCGATCTCTCCAC-CAAAG-3", 5"-GGGTCAGCACGTTTGTCATTG-3") and probe (5"-Fam-TGCCCGACCATGGGAGAAGCT-Tamra-3") targeted a region within the envelope gene of the WNV genomic RNA. RNA equivalents were finally determined from a standard curve based on a RNA preparation of known concentration which was serially diluted in cell lysates of negative control cells and purified according to the same protocol.

The RNA content in supernatants of transfected cells was measured as recently published in Orlinger, K. K. et al. (2006). Accordingly, prior to quantification by real-time PCR, aliquots of supernatants were cleared by low-speed centrifugation and RNA was purified by using the QIAamp viral RNA Mini kit (QIAGEN) as suggested by the manufacturer. RNA export was finally calculated by determining the ratio between RNA equivalents in supernatants and those of total RNA preparations which comprise both intracellular and extracellular RNA.

Cytotoxicity assay. Similar to the RNA replication and export experiments, Vero cells were seeded into 6-well plates and infected with WNV stock preparations at a MOI of 1.0, with the exception that the growth medium did not contain BSA. Aliquots of supernatants were transferred into 96-well plates and cytotoxicity was assessed by measuring the release of lactate dehydrogenase (LDH) using the CytoTox 96 Non-Radioactive Cytotoxicity Assay (Promega) according to manufacturer's instructions.

Plaque morphology and immunocytochemistry. Vero cells were grown to 80% confluence in 12-well plates and incubated for 1 h with virus suspensions serially diluted in infection medium. The cells were subsequently overlaid with EMEM containing 5% FBS, 1.5% glutamine, 1% penicillin/streptomycin, 15 mM HEPES and 0.25% agarose (Sigma). The plaque morphology was determined following an incubation period ranging from 4 to 6 days post infection. Thus, cells were fixed and stained with a solution containing 4% formaldehyde and 0.1% crystal violet.

Infectious or focus forming units (FFU) were determined by immunocytochemistry. Subsequent to incubation for 2 to 4 days, the agarose overlay was removed and cells were fixed with 1:1 acetone/methanol. The cells were rehydrated with PBS pH 7.4 containing 5% sheep serum for 30 min at room temperature. Subsequently, the cells were incubated for 1 h at 37° C. with a WNV specific polyclonal antiserum (gamma-WN/KIS/2), diluted 1:3000 in PBS pH 7.4 with 0.2% Tween and 3% sheep serum. Cells were washed twice with PBS pH 7.4 containing 0.2% Tween and 3% sheep serum and once with TBS buffer (137 mM sodium chloride, 3 mM potassium chloride, 25 mM Tris pH 8.0) containing 0.2% Tween and 3% sheep serum. The incubation with a 1:400 dilution of an anti-rabbit alkaline phosphatase conjugated secondary antibody was performed in TBS buffer with 0.2% Tween and 3% sheep serum for 45 min at room temperature. Following two washes with the same buffer, WNV specific foci were detected by incubating with SIGMAFAST™ Fast Red TR/Naphthol AS-MX for 10 min.

Results

RNA export and specific infectivity of mutants CD36 and CD37 are moderately reduced compared to wild-type WNV. Despite lacking more than one third of protein C including large parts of the entire hydrophobic domain, mutants CD36 and CD37 were found to be infectious and genetically stable. To characterize their capacity to replicate, export and infect in detail, quantitative tests were performed in comparison with the wild-type virus. Vero cells were infected with virus stocks ($1 \times 10^7$ FFU/ml) at a MOI of 1, and both intracellular RNA synthesis and RNA export into the supernatant were assessed by real-time quantitative PCR (qPCR). As shown in FIG. 3A, intracellular RNA replication of both mutants was similar to wild-type at 24 and 48 h postinfection. At 72 and 96 h postinfection, intracellular RNA values of mutant CD37 were still at wild-type levels whereas that of mutant CD36 decreased. This decrease was accompanied by strong CPE causing a strong reduction of cell numbers at these time points. To confirm the visually observed CPE, cytotoxicity was quantitatively assessed by measuring the release of lactate dehydrogenase (LDH) into the supernatants of infected cells. As shown in FIG. 3E, LDH release from cells infected with mutant CD36 was in the same range as wild-type and mutant CD37 until 48 h postinfection. In contrast, at the later timepoints, LDH levels in supernatants of CD36 infected cells were significantly higher than others thus confirming its high cytotoxicity and suggesting that the decreased intracellular RNA values for CD36 at 72 and 96 h postinfection were indeed a consequence of excessive cell deaths (compare FIGS. 3A and 3E).

Quantification of RNA release into the supernatants revealed moderate differences between protein C deletion mutants and wild-type virus. Mutants CD36 and particularly CD37 released less viral RNA than wild-type into the supernatant at 24 h postinfection (FIG. 3B). However, whereas CD37 achieved wild-type levels at later time points, CD36 remained approximately one order of magnitude below the wild-type control at all times with values decreasing after 48 h, presumably due to the above described loss of producing cells caused by this mutant's prominent cytotoxicity. To better compare the export efficiency of mutant and wild-type RNA, the percentage of total (extracellular and intracellular) RNA equivalents which was released into the supernatant was calculated for the 48 h time point, at which time effects of cytotoxicity were still low and comparable among the samples. As illustrated in FIG. 3C, export efficiency of mutants CD36 and CD37 were about two third and half of the wild-type value indicating that the mutated capsid proteins, although clearly less efficient in packaging of RNA and/or assembly of virions, were still able to facilitate the export of a significant percentage of the total RNA from infected cells. To further determine the export of viral particles, the same supernatants as used for the quantification of viral RNA were subjected to hemagglutination assay. As shown in FIG. 3D, the results of this analysis were in good agreement with the RNA data shown in FIG. 3B. For mutant CD37, the release of viral particles was delayed, but reached nearly wild-type level at the latest time point. In contrast, mutant CD36 remained below wild-type by approximately 3 log 2 dilutions (i.e. approximately 8-fold) at all times, similar to the approximately 10-fold difference observed in the RNA values.

To quantitatively compare the specific infectivity of mutant and wild-type viruses, virus preparations were subjected to qPCR to determine the number of RNA equivalents (presumed to correlate to the number of virions) and focus assays to quantify infectious units in these preparations. The ratio of RNA equivalents to FFU was then calculated and results are plotted in FIG. 3F. Whereas this ratio was approximately 10 for wild-type virus (i.e. one out of 10 RNA equivalents/virions caused an infectious focus), it was between 10 and 100-fold higher in the case of the two deletion mutants indicating reduced specific infectivity.

In conclusion, the quantitative comparisons indicated moderate, but significant impairments of both viral export and entry caused by the deletion mutations.

Growth properties of viral particles in cell culture. An altered plaque and focus morphology is a good indicator for changes regarding virulence. Therefore, the capacity of mutants CD37 and CD36 to form plaques on a Vero cell monolayer was assessed. After incubation for 6 days, however, no plaques could be identified for both mutants whereas wild-type virus plaques reached a plaque size between 8 and 15 mm (12.6+/−2.4 mm, Table 2). In contrast, all mutants were capable of forming foci on a Vero cell monolayer. These were however at least 4 times smaller when compared to wild type foci (Table 2).

The impaired plaque formation as well as the reduced focus size of mutants CD37 and CD36 already suggested already an attenuated phenotype. To investigate cell culture growth in more detail, the specific infectivity was determined, i.e. the ratio of RNA equivalents to infectious particles as determined by immunocytochemistry. As shown in FIG. 3F, the specific infectivity was significantly reduced for both mutants or, in other words, more RNA equivalents were necessary to produce 1 infectious unit (FFU).

To summarize, the WNV capsid deletion mutants show altered growth properties in cell culture than wild-type. The observed growth properties in cell culture are important as they are a good indicator for an attenuated phenotype in the animal model.

Example 3

Large Deletion Mutants as Live Attenuated Vaccines

Experimental Procedures

Animal model. To establish the animal model, 4-weeks-old female BALB/c mice were inoculated intraperitoneally (i.p) with different doses of WNV wild-type virus. The dilutions were performed in cell culture media which was also used as a negative control. Following infection, survival of animals was monitored for 28 days. The dose at which 50% of animals succumbed to infection (LD50) provided the basis for calculation of the challenge dose, which was set to a 100-fold LD50.

In vivo characterization of mutant viruses. To characterize the virulence and immunogenicity of mutant viruses, 4-weeks-old female BALB/c mice were inoculated intraperitoneally (i.p.) with serial dilutions of WNV stock preparations. Wild-type virus and cell culture medium were used as positive and negative controls, respectively. Following an observation period of 4 weeks, blood was taken from surviving mice via tail vein. Seroconversion was detected by ELISA as described in Heinz et al. (1983) except that 50 µl of 0.25 µg/ml formalin inactivated WNV was used for coating of plates. To test whether seroconverted mice had developed protective immunity, the mice were inoculated with a challenge dose of the wild-type strain (see below). Survival was recorded for 4 weeks post challenge.

Results

Animal model. To establish the animal model, groups of 10 4-weeks old female BALB/c mice were inoculated intraperitoneally with serial dilutions of wild-type WNV. Lethally infected mice succumbed to infection between 7 and 10 days post infection. As shown in Table 3, in the two high dosage groups (50 and 500 FFU), none of the animals survived. In contrast, when mice were inoculated with 5 and 0.5 FFU, 8 out of 10 and 7 out of 9 mice survived the infection with wild-type virus, respectively. When 0.05 FFU of wild-type virus was applied, none of the animals was lethally infected. In addition, all animals of the negative control group survived. Interestingly, all surviving animals did not show any signs of disease. To summarize, these data indicated that survival was indeed dose dependent. Furthermore, the reliability of the animal model was confirmed.

The dose at which 50% of animals succumb to infection (LD50) is an important parameter for assessing the virulence of a virus. Furthermore, this parameter allows the calculation of the challenge dose for immunization studies, which is typically set to a 100-fold LD50. For the experiment shown in Table 3, the LD50 lies between 5 and 50 FFU. Consequently, the approximate 100-fold LD50 or challenge dose corresponded to $10^3$ FFU.

Testing of vaccine candidates in the animal model. To test mutants CD37 and CD36 in the animal model, 4-weeks old female BALB/c mice were immunized with different doses of both vaccine candidates. Upon peripheral inoculation, virulent neuroinvasive WNV strains cause lethal encephalitis in almost all infected animals, whereas attenuated strains cause symptomless infections that induce a specific antibody response. For each candidate, 7 groups of 10 animals per group were tested by applying doses ranging form 100 to $10^6$ FFU. As shown in Table 3, all animals survived even when mice were inoculated with high doses of the vaccine candidates. As a consequence, the LD50 was >$10^6$ FFU. Furthermore, none of the animals showed any signs of disease; this implies a low virulence for mutants CD37 and CD36.

4 weeks post infection, seroconversion of vaccinated animals was assessed by WNV specific ELISA as described in the experimental procedures section. To test whether immunization with mutants CD37 and CD36 resulted in a protective immune response, animals were challenged with a lethal dose of wild-type virus ($10^3$ FFU). As shown in Table 3, seroconversion correlated well with protection.

To summarize, the low virulence and protective potential of both CD37 and CD36 were clearly demonstrated.

TABLE 1

WNV capsid deletion mutants.

| Designation | Deleted aa[a] | Additional Mutation | Compensating Mutation | Genetic stability[b] | Virus Stocks FFU/ml |
|---|---|---|---|---|---|
| wild-type | | | | + | >$10^8$ |
| CD7/3 | F53-I59 | | | − | nd[c] |
| CD7/3 + R45L | F53-I59 | | R45L | + | >$10^6$ |
| CD10 | I44-F53 | | | − | nd[c] |
| CD37 | L51-E87 | | | + | >$10^7$ |
| CD36 | G40-Q75 | D39E[d] | | + | >$10^7$ |

[a]The first and last deleted amino acids (aa) are listed.
[b]The genetic stability was examined by performing end-point passages and sequence analysis.
[c]The production of virus stocks was not possible as further mutations rapidly emerged. FFU (focus forming units).
[d]The additional mutation is a result of the shift in codons caused by the deletion of the nucleic acids.

TABLE 2

Plaque and focus morphology of wild-type WNV and stable mutants.

| | Morphology | |
|---|---|---|
| Virus | Mean plaque size in mm[a] | Mean focus size in mm[b] |
| wild-type | 12.6 +/− 2.4 | 19.8 +/− 2.86 |
| CD37 | — | 5.05 +/− 1.07 |
| CD36 | — | 2.85 +/− 0.63 |

[a]Mean plaque size was determined at day 6 post infection. None of the capsid deletion mutants induced plaque formation, even when incubation was prolonged to 9 days post infection.
[b]Mean focus size was determined at day 6 post infection.

TABLE 3

In vivo evaluation of wild-type and mutant WNV

| Virus | Dose FFU[a] | Surviving mice pI | Seroconv. pI[b] | Surviving mice pCH[c] | LD50 |
|---|---|---|---|---|---|
| wild-type | 0.05 | 10/10 | 0/10 | n.a.[f] | 5-50 |
| | 0.5 | 7/9[d] | 0/7 | n.a.[f] | |
| | 5 | 8/10 | 0/8 | n.a.[f] | |
| | 50 | 0/10 | n.a.[f] | n.a.[f] | |
| | 500 | 0/10 | n.a.[f] | n.a.[f] | |
| CD37 | 0 | 10/10 | 2/10 | 4/10 | >$10^6$ FFU |
| | 1 | 10/10 | 5/10 | 8/10 | |
| | 2 | 10/10 | 9/10 | 10/10 | |
| | 3 | 10/10 | 10/10 | 10/10 | |
| | 4 | 10/10 | 10/10 | 10/10 | |
| | 5 | 10/10 | 10/10 | 10/10 | |
| | 6 | 10/10 | 10/10 | 9/9[d] | |
| CD36 | 0 | 10/10 | 3/10 | 4/10 | >$10^6$ FFU |
| | 1 | 10/10 | 9/10 | 9/10 | |
| | 2 | 10/10 | 10/10 | 10/10 | |
| | 3 | 10/10 | 10/10 | 10/10 | |
| | 4 | 10/10 | 10/10 | 10/10 | |
| | 5 | 10/10 | 10/10 | 10/10 | |
| | 6 | 10/10 | 10/10 | 10/10 | |
| neg. control | n.a.[f] | 10/10 | 0/10 | 0-2[e]/10 | n.a.[f] |

[a]For clarity, the dose is shown in logarithmic scale for mutants CD37 and CD36.
[b]Seroconversion was exclusively determined for surviving mice.
[c]Challenge was performed for all animals with the exception of wild-type infected mice.
[d]One mouse was killed in an accident.
[e]In two out of three experiments, two mice of the negative control group survived the challenge with a 100-fold LD50 dose wild-type virus.
[f]not applicable

Example 4

Characterization of a Mutant Lacking 48 Amino Acids (CD48)

Experimental Procedures

Mutant construction. In mutant CD48, deletions of mutants CD37 and CD36 were combined. Accordingly, CD48 included the D39E mutation and a deletion including residues G40 to E87. The construction was performed using standard cloning procedures (see also Example 1).

Mutant stability. Mutant stability was assessed as described in the experimental procedures section of Example 1.

Results

Characterization of mutant CD48. This mutant lacks 48 amino acids ranging from residues G40 to E87. Furthermore, mutant CD48 includes the D39E mutation which was identified within mutant CD36. Passaging experiments with mutant CD48 however revealed that this mutant is unstable. Thus, a rapidly emerging duplication of residues flanking the 48 amino acid deletion, i.e. M16 to D39E and L88 to A94, was identified. Although this duplication slightly improved cell culture growth properties, the production of a stable, high titer stock was still not possible. This result indicates that the number of amino acid residues which can be deleted without severely reducing the growth properties in cell culture is limited. Thus, deletions of approximately one third of the capsid protein are well tolerated whereas a 48 amino acid deletion severely impairs protein function and requires additional mutations (such as the observed duplication) to regain the ability to be passaged in cell culture.

Example 5

Secondary Structure Predictions for Selected WNV Capsid Deletion Mutants

Experimental Procedures

Secondary structure predictions: Secondary structure predictions were performed using PsiPred (Jones, D. T. 1999) and pepcoil (Emboss software package; Rice, P. et al., 2000) using a window size of 10.

Results

Location of deletions on the WNV (subtype Kunjin) 3D structure. Recently, the crystal structure of the WNV capsid protein (Kunjin subtype) has been solved (Dokland, T. et al., 2004; Protein Data Bank accession code 1SFK). The WNV capsid protein is composed of four alpha helices; in the crystal structure, the protein forms dimers that are organized into tetramers. Each dimer resembles a three layered structure with helices alpha 1 on top, helices alpha 2 in the middle and helices alpha 4 at the bottom; in contrast, helix alpha 3 is not organized pairwise and seems to serve as spacer instead. One might assume that the introduction of large deletions might disturb the overall conformation of the protein and impair protein function. Interestingly, such large deletions were identified, i.e. CD37 and CD36; nevertheless, these truncated proteins were capable of forming infectious virus particles and producing high-titer, stable virus stocks.

To elucidate the structural consequences of these large deletions, their location within the WNV crystal structure was investigated using PyMOL software (DeLano, W. L., DeLano Scientific, San Carlos, Calif., 2002). Mutant CD37 lacks approximately half of helix alpha 2, the entire helix alpha 3 and approximately half of helix alpha 4. One might assume that, as a consequence, the remainders of helix alpha 2 and helix alpha 4 are fused thereby forming two layers instead of three. Stacking of the two-layered structure might nevertheless enable multimer formation and capsid assembly. Similarly, removal of helices alpha 2 and alpha 3 in mutant CD36 might result in the formation of a two-layered structure, as the top layer of helices alpha 1 and the bottom layer of helices alpha 4 remain more or less unaffected.

In contrast, mutant CD48 lacks helix alpha 2, helix alpha 3 and approximately half of helix alpha 4. As stated in Example 4, this mutant was severely impaired in its growth properties. This impaired cell culture growth properties of mutant CD48 can be explained by the finding that helix alpha 1, which was unaffected by the deletion, and helix alpha 4, which was reduced to two turns, are incapable of forming a two-layered structure.

To summarize, the common features of mutants CD36 and CD37 are that the entire helix alpha 3 and parts of helix alpha 4 were removed, whereas helix alpha 1 remained unchanged. On the basis of close examination of the crystal structure, it is found that the removal of the helical inner layer results in a two-layered structure which is nevertheless functional. In contrast, in the CD48 mutant, formation of a two-layered structure was found to be impaired.

Secondary structure prediction. To investigate the structural impacts in more detail, secondary structure prediction analysis was performed (PsiPred Jones, D. T. 1999). First, the reliability of the predictions was evaluated by comparing the WNV (Kunjin subtype) sequence with the corresponding crystal structure (Dokland, T. et al., 1997). As shown in FIG. 5A, the secondary prediction and the crystal structure fitted very well; it is import to note that only residues also present in the crystal structure were analyzed. FIG. 5B shows the secondary structure prediction for the isolate used in this analysis. Here, the entire capsid protein sequence was analyzed, i.e. M1 to A123. Similar to the analysis of the Kunjin sequence, the four internal helices alpha 1 to alpha 4 were predicted (compare FIG. 5A and FIG. 5B); furthermore, a large helix was predicted for the very C-terminal end. This helix corresponds to the signal sequence which is cleaved off by the viral NS2/B3 protease during virus maturation.

In FIG. 5C, the secondary structure prediction for mutant CD7/3 is shown. As stated before (Example 1), this mutant was constructed by the introduction of a 7 amino acid deletion into helix alpha 2 of the capsid protein. As a consequence, helix alpha 2 was significantly shortened, which was also observed by the secondary structure predictions for the CD7/3 mutant sequence (compare FIG. 5B with FIG. 5C). Instead of the four helices predicted for mutant CD7/3, however, removal of 30 additional residues in CD37 resulted in the formation of two helices with the latter one composed of the remainder of helices alpha 2 and 4 (compare FIG. 5C and FIG. 5D). It is important to note that, when compared to the lower confidence values of helix alpha 2 in the CD7/3 mutant, the confidence value for the prediction of this alpha 2/4 fusion helix has increased. This indicates that the structure of the protein has been stabilized by the removal of the additional 30 amino acid residues.

The secondary structure prediction for mutant CD10 (FIG. 5E) suggested that the remainder of helix alpha 2 was replaced by a long stretch of coiled residues. This region might interfere with protein stability. In contrast, the 36 amino acid deletion in the CD36 mutant resulted in complete removal of helices alpha 2 and 3. The secondary structure prediction suggested one large single alpha helix (FIG. 5F)

which resulted from fusion of helices alpha 1 and alpha 4. Importantly, low confidence values are observed for a few residues in the N-terminal part of this fusion helix. This indicates that alternatively two helices are formed, which would support the hypothesis of the importance of the two-layered structure (see previous section). On the other hand, one might as well assume that a single large fusion helix is also capable of participating in helix stacking and capsid protein assembly.

In FIG. 5G, the secondary structure prediction for mutant CD48 is shown. Helix alpha 1 and the remainders of helix alpha 4 might form a fusion helix; the corresponding confidence values were however low and suggested that the structure is somewhat instable. In contrast, the duplication of residues M16-E39/L88-A94 in mutant CD48 duplication might result in the formation of two helices with higher confidence values (compare FIG. 5G with FIG. 5H). These two helices might, similar to those for mutants CD37 and CD36, form a two-layered structure and participate in the stacking process. In addition, mutants CD48 and CD48 duplication were analyzed by using the pepcoil program (Emboss software package; Rice, P. et al., 2000). Interestingly, for mutant CD48, a coiled coil structure was predicted (FIG. 5G); the duplication in mutant CD48 possibly results in the formation of two coiled coils thereby supporting the hypothesis of their involvement in the helix stacking process (FIG. 5H). It is important to note that coiled coils were also predicted for residues L30 to D39 and K85 to N96 in the wild-type sequence; interestingly, two coiled coils were also predicted for all other investigated mutants with the exception of mutant CD48.

To summarize, secondary structure prediction for mutants CD7/3 and CD10 suggested that the introduced deletions destabilize the capsid protein. The removal of additional residues in mutants CD37 and CD36 seemed to improve protein stability as indicated by close examination of the 3D structure as well as secondary structure predictions. In contrast, the deletion present in mutant CD48 resulted in the formation of a single, less stable helix and the stabilization of the mutant was dependent on the acquaintance of a duplication. Furthermore, as emphasized by comparison of mutants CD48 and CD48 duplication, the presence of helices capable of forming two coiled coils is important.

Example 6

Comparison of the WNV and Dengue Virus Sequence and Structure

Experimental Procedures

Sequence conservation. The sequence conservation was assessed by using BLAST (Altschul S. F. et al., 1997).

Results

Homology of WNV and Dengue virus capsid proteins. To date, two 3D structures of flaviviral capsid proteins have been solved, i.e. the crystal structure of the Kunjin subtype of WNV and the solution structure of the Dengue virus capsid protein (Dokland, T. et al., 2004; Ma, L. et al., 2004). As the Kunjin capsid protein, the Dengue virus capsid protein is composed of four helices and forms dimers. Interestingly, both structures superimpose relatively well (Dokland, T. et al., 2004) thereby indicating that the fold might be conserved between flaviviral capsid proteins. In addition, this finding suggests that the principle described in Examples 1 to 5 for the WNV NY99 isolate can be applied for other flaviviruses as well. To further support this hypothesis, the sequences of the WNV NY99 isolate was compared with that of WNV subtype Kunjin and Dengue virus by using BLAST (Altschul, S. F. et al., 1997). As shown in FIGS. 6A and 6B, WNV NY99 shares 94% and 42% identical residues with WNV subtype Kunjin and Dengue virus, respectively. The homology of the investigated capsid proteins was further underlined, when residues that are not identical but highly conserved were included in the analysis. Accordingly, the sequence homology of WNV NY99 with WNV subtype Kunjin and Dengue was 96% and 62% respectively.

To summarize, the examination of the 3D structures and the assessment of the sequence homology suggested that the flaviviral capsid proteins adopt a highly conserved fold. This indicates that large deletion mutants with beneficial properties might be constructed for other flaviviruses, e.g. Dengue virus as well.

REFERENCES

The following references which have been recited in the specification are incorporated herein by reference in their entirety.

1. Bjorklund et al. 1998. Virus Genes 16:307-312.
2. Butrapet et al. 2000. J. Virol. 74:3011-3019.
3. Guirakhoo et al. 2000. J. Virol. 74:5477-5485.
4. Hall et al. 1999. Virology 264:66-75.
5. Hope et al. 2000. J. Gen. Virol. 81:1913-1925.
6. Hopp et al. 1981. PNAS 78:3824-3828.
7. Khromykh et al. 1996. Arch. Virol. 141:685-699.
8. Khromykh et al. 1997. J. Virol. 71:1497-1505.
9. Kyte et al. 1982. J. Mol. Biol. 157:105-132.
10. Lai et al. 1998. Clin Diagn. Virol. 10:173-179.
11. Mandl et al. 2000. J. Virol. 74:9601-9609.
12. Mandl et al. 1998. J. Virol. 72: 2132-2140.
13. Markoff et al. 1997. Virology 233:105-117.
14. McMinn. 1997. J. Gen. Virol. 78:2711-2722.
15. Meyers et al. 1999. J. Virol. 73:10224-10235.
16. Nitayaphan et al. 1990. Virology 177:541-552.
17. Post et al. 1992. Virology 188:160-167.
18. Xie et al. 1998. J. Gen. Virol. 79:1895-1899.
19. Altschul, S. F. et al. 1997. Nucleic Acid Res 25: 3389-402.
20. Bolivar, F. et al. 1977. Gene 2: 95-113.
21. Dokland, T. et al. 2004. Structure 12: 1157-63.
22. Elshuber, S. et al. 2003. J Gen Virol 84: 183-91.
23. Guirakhoo, F. et al. 1989. Virology 169: 90-9.
24. Heinz, F. X. et al. 1983. Virology 126: 525-37.
25. Jones, D. T. 1999. J Mol Biol 292:195-202.
26. Kofler, R. M. et al. 2002. J Virol 76: 3534-43.
27. Kofler, R. M. et al. 2003. J Virol 77: 443-51.
28. Kofler, R. M. et al. 2006. J Virol 80: 4099-113.
29. Ma, L. et al. 2004. PNAS 101: 3414-9.
30. Mandl, C. W. et al. 1997. J Gen Virol 78: 1049-57.
31. Orlinger, K. K. et al. 2006. J Virol 80: 12197-208.
32. Rice, P. et al. 2000. Trends in Genetics 16: 276-7.
33. Varnayski, A. N. et al. 2000. J Virol 74: 4394-403.
34. Clarke, D. H. and Casals, J. 1958. Am J Trop Med Hyg 7: 561-73.

The invention claimed is:

1. A mutant virus of the flavivirus genus, comprising a capsid protein with a deletion of up to 47 amino acids, wherein the deletion comprises the entire helix 3, and wherein there are no further deletion, substitution or insertion mutations within the capsid protein, with the proviso that amino acids adjacent to the deletion may be substituted.

2. The virus of claim 1, further defined as an arthropod borne virus.

3. The virus of claim 2, further defined as a mosquito borne virus.

4. The virus of claim 1, further defined as yellow fever virus (YFV), Japanese encephalitis virus (JEV), Dengue viruses (DV), tick-borne encephalitis virus (TBE virus), West Nile virus (WNV), Murray Valley encephalitis virus (MVEV), Saint Louis encephalitis virus (SLEV) or Powassan virus (PV).

5. The virus of claim 1, wherein the deletion is of at least 22 successive amino acids.

6. The virus of claim 5, wherein the deletion is of at least 24 successive amino acids.

7. The virus of claim 6, wherein the deletion is of at least 26 successive amino acids.

8. The virus of claim 7, wherein the deletion is of at least 28 successive amino acids.

9. The virus of claim 8, wherein the deletion is of at least 30 successive amino acids.

10. The virus of claim 9, wherein the deletion is of at least 32 successive amino acids.

11. The virus of claim 10, wherein the deletion is of at least 34 successive amino acids.

12. The virus of claim 1, wherein the deletion is of up to 46 amino acids.

13. The virus of claim 12, wherein the deletion is of up to 44 amino acids.

14. The virus of claim 13, wherein the deletion is of up to 42 amino acids.

15. The virus of claim 14, wherein the deletion is of up to 40 amino acids.

16. The virus of claim 15, wherein the deletion is of up to 38 amino acids.

17. The virus of claim 1, wherein the virus is capable of being passaged in cell culture and genetically stable.

18. The virus of claim 17, wherein virus is capable of being passaged at least two times in cell culture.

19. The virus of claim 1, wherein the deletion comprises at least one amino acid of alpha helix 2 of the wild type virus capsid protein.

20. The virus of claim 19, wherein the deletion comprises at least a third of the amino acids of helix 2.

21. The virus of claim 20, wherein the deletion comprises the C-terminal amino acids of helix 2.

22. The virus of claim 1, wherein the deletion comprises at least one amino acid of alpha helix 4 of the wild type virus capsid protein.

23. The virus of claim 22, wherein the deletion comprises at least one third of the amino acids of helix 4.

24. The virus of claim 23, wherein the deletion comprises the N-terminal amino acids of helix 4.

25. The virus of claim 1, further defined as comprising a mutation outside of the capsid protein.

26. A pharmaceutical composition comprising the virus of claim 1, a capsid protein of that mutated virus, or a nucleic acid encoding a capsid protein of the mutated virus.

27. The pharmaceutical composition of claim 26, further defined as a vaccine.

28. The pharmaceutical composition of claim 26, further defined as comprising $10^1$ to $10^7$ infectious units of said virus.

29. The pharmaceutical composition of claim 28, further defined as comprising $10^2$ to $10^6$ infectious units of said virus.

30. The pharmaceutical composition of claim 29, further defined as comprising $10^3$ to $10^5$ infectious units of said virus.

31. The pharmaceutical composition of claim 26, further defined as comprising antibiotics, preservatives, stabilizers, buffer substances or mixtures thereof.

32. The pharmaceutical composition of claim 26, further defined as comprising an aminoglycoside antibiotic, a liposome, a microsphere or a mixture thereof.

33. The pharmaceutical composition of claim 32, wherein the aminoglycoside antibiotic is neomycin or kanamycin.

34. The virus of claim 1, wherein the deletion comprises the entire helix 2.

* * * * *

SEQUENCE LISTING

<160> NUMBER OF SEQ ID NOS: 24

<210> SEQ ID NO 1
<211> LENGTH: 115
<212> TYPE: PRT
<213> ORGANISM: Tick-borne encephalitis virus

<400> SEQUENCE: 1

Val Lys Lys Ala Ile Leu Lys Gly Lys Gly Gly Pro Pro Arg Arg
1               5                   10                  15

Val Ser Lys Glu Thr Ala Thr Lys Thr Arg Gln Pro Arg Val Gln Met
                20                  25                  30

Pro Asn Gly Leu Val Leu Met Arg Met Met Gly Ile Leu Trp His Ala
            35                  40                  45

Val Ala Gly Thr Ala Arg Asn Pro Val Leu Lys Ala Phe Trp Asn Ser
        50                  55                  60

Val Pro Leu Lys Gln Ala Thr Ala Ala Leu Arg Lys Ile Lys Arg Thr
65                  70                  75                  80

Val Ser Ala Leu Met Val Gly Leu Gln Lys Arg Gly Lys Arg Arg Ser
                85                  90                  95

Ala Thr Asp Trp Met Ser Trp Leu Leu Val Ile Thr Leu Leu Gly Met
            100                 105                 110

Thr Leu Ala
        115

<210> SEQ ID NO 2
<211> LENGTH: 124
<212> TYPE: PRT
<213> ORGANISM: West Nile virus

<400> SEQUENCE: 2

Ser Lys Lys Pro Gly Gly Pro Gly Lys Asn Arg Ala Val Asn Met Leu
1               5                   10                  15

Lys Arg Gly Met Pro Arg Gly Leu Ser Leu Ile Gly Leu Lys Arg Ala
                20                  25                  30

Met Leu Ser Leu Ile Asp Gly Lys Gly Pro Ile Arg Phe Val Leu Ala
            35                  40                  45

Leu Leu Ala Phe Phe Arg Phe Thr Ala Ile Ala Pro Thr Arg Ala Val
        50                  55                  60

Leu Asp Arg Trp Arg Gly Val Asn Lys Gln Thr Ala Met Lys His Leu
65                  70                  75                  80

Leu Ser Phe Lys Lys Glu Leu Gly Thr Leu Thr Ser Ala Ile Asn Arg
                85                  90                  95

Arg Ser Thr Lys Gln Lys Lys Arg Gly Gly Thr Ala Gly Phe Thr Ile
            100                 105                 110

Leu Leu Gly Leu Ile Ala Cys Ala Leu Leu Ser Lys
        115                 120

<210> SEQ ID NO 3
<211> LENGTH: 113
<212> TYPE: PRT
<213> ORGANISM: Dengue virus

<400> SEQUENCE: 3

Asn Asp Gln Arg Lys Lys Ala Arg Asn Thr Pro Phe Asn Met Leu Lys
1               5                   10                  15

Arg Glu Arg Asn Arg Val Ser Thr Val Gln Gln Leu Thr Lys Arg Phe

```
                    20                  25                  30
Ser Leu Gly Met Leu Gln Gly Arg Gly Pro Leu Lys Leu Phe Met Ala
            35                  40                  45

Leu Val Ala Phe Leu Arg Phe Leu Thr Ile Pro Pro Thr Ala Gly Ile
 50                  55                  60

Leu Lys Arg Trp Gly Thr Ile Lys Lys Ser Lys Ala Ile Asn Val Leu
 65                  70                  75                  80

Arg Gly Phe Arg Lys Glu Ile Gly Arg Met Leu Asn Ile Leu Asn Arg
                 85                  90                  95

Arg Arg Arg Thr Ala Gly Met Ile Ile Met Leu Ile Pro Thr Val Met
            100                 105                 110

Ala
```

```
<210> SEQ ID NO 4
<211> LENGTH: 99
<212> TYPE: PRT
<213> ORGANISM: classical porcine fever virus

<400> SEQUENCE: 4

Ser Asp Asp Gly Ala Ser Gly Ser Lys Asp Lys Pro Asp Arg Met
1               5                   10                  15

Asn Lys Gly Lys Leu Lys Ile Ala Pro Arg Glu His Glu Lys Asp Ser
            20                  25                  30

Lys Thr Lys Pro Pro Asp Ala Thr Ile Val Val Glu Gly Val Lys Tyr
         35                  40                  45

Gln Ile Lys Lys Lys Gly Lys Val Lys Gly Lys Asn Thr Gln Asp Gly
     50                  55                  60

Leu Tyr His Asn Lys Asn Lys Pro Pro Glu Ser Arg Lys Lys Leu Glu
 65                  70                  75                  80

Lys Ala Leu Leu Ala Trp Ala Val Ile Thr Ile Leu Leu Tyr Gln Pro
                 85                  90                  95

Val Ala Ala
```

```
<210> SEQ ID NO 5
<211> LENGTH: 102
<212> TYPE: PRT
<213> ORGANISM: Bovines virales Diarrhoe Virus

<400> SEQUENCE: 5

Ser Asp Thr Lys Glu Glu Gly Ala Thr Lys Lys Thr Gln Lys Pro
1               5                   10                  15

Asp Arg Leu Glu Arg Gly Lys Met Lys Ile Val Pro Lys Glu Ser Glu
            20                  25                  30

Lys Asp Ser Lys Thr Lys Pro Pro Asp Ala Thr Ile Val Val Glu Gly
         35                  40                  45

Val Lys Tyr Gln Val Arg Lys Lys Gly Lys Thr Lys Ser Lys Asn Thr
 50                  55                  60

Gln Asp Gly Leu Tyr His Asn Lys Asn Lys Pro Gln Glu Ser Arg Lys
 65                  70                  75                  80

Lys Leu Glu Lys Ala Leu Leu Ala Trp Ala Ile Ile Ala Ile Val Leu
                 85                  90                  95

Phe Gln Val Thr Met Gly
                 100
```

```
<210> SEQ ID NO 6
<211> LENGTH: 100
<212> TYPE: PRT
```

-continued

<213> ORGANISM: Border Disease Virus

<400> SEQUENCE: 6

Ser Asp Asp Asn Lys Asn Glu Lys Thr Asn Glu Lys Lys Pro Asp Arg
1               5                   10                  15

Val Lys Arg Gly Ala Met Lys Ile Thr Pro Lys Glu Ser Glu Lys Asp
            20                  25                  30

Ser Lys Ser Lys Pro Pro Asp Ala Thr Ile Val Val Asp Gly Val Lys
        35                  40                  45

Tyr Gln Val Lys Lys Gly Lys Val Lys Ser Lys Asn Thr Gln Asp
    50                  55                  60

Gly Leu Tyr His Asn Lys Asn Lys Pro Pro Glu Ser Arg Lys Lys Leu
65              70                  75                  80

Glu Lys Ala Leu Leu Ala Trp Ala Val Leu Ala Val Leu Met Trp Gln
                85                  90                  95

Pro Val Lys Pro
            100

<210> SEQ ID NO 7
<211> LENGTH: 190
<212> TYPE: PRT
<213> ORGANISM: Hepatitis C Virus 1

<400> SEQUENCE: 7

Ser Thr Asn Pro Lys Pro Gln Lys Lys Asn Lys Arg Asn Thr Asn Arg
1               5                   10                  15

Arg Pro Gln Asp Val Lys Phe Pro Gly Gly Gly Gln Ile Val Gly Gly
            20                  25                  30

Val Tyr Leu Leu Pro Arg Arg Gly Pro Arg Leu Gly Val Arg Ala Thr
        35                  40                  45

Arg Lys Thr Ser Glu Arg Ser Gln Pro Arg Gly Arg Arg Gln Pro Ile
    50                  55                  60

Pro Lys Ala Arg Arg Pro Glu Gly Arg Thr Trp Ala Gln Pro Gly Tyr
65              70                  75                  80

Pro Trp Pro Leu Tyr Gly Asn Glu Gly Cys Gly Trp Ala Gly Trp Leu
                85                  90                  95

Leu Ser Pro Arg Gly Ser Arg Pro Ser Trp Gly Pro Thr Asp Pro Arg
            100                 105                 110

Arg Arg Ser Arg Asn Leu Gly Lys Val Ile Asp Thr Leu Thr Cys Gly
        115                 120                 125

Phe Ala Asp Leu Met Gly Tyr Ile Pro Leu Val Gly Ala Pro Leu Gly
    130                 135                 140

Gly Ala Ala Arg Ala Leu Ala His Gly Val Arg Val Leu Glu Asp Gly
145                 150                 155                 160

Val Asn Tyr Ala Thr Gly Asn Leu Pro Gly Cys Ser Phe Ser Ile Phe
                165                 170                 175

Leu Leu Ala Leu Leu Ser Cys Leu Thr Val Pro Ala Ser Ala
            180                 185                 190

<210> SEQ ID NO 8
<211> LENGTH: 190
<212> TYPE: PRT
<213> ORGANISM: Hepatitis C Virus 2

<400> SEQUENCE: 8

Ser Thr Asn Pro Lys Pro Gln Arg Lys Thr Lys Arg Asn Thr Asn Arg
1               5                   10                  15

Arg Pro Gln Asp Val Lys Phe Pro Gly Gly Gln Ile Val Gly
            20                  25                  30

Val Tyr Leu Leu Pro Arg Arg Gly Pro Arg Leu Gly Val Arg Ala Thr
                35                  40                  45

Arg Lys Thr Ser Glu Arg Ser Gln Pro Arg Gly Arg Arg Gln Pro Ile
 50                  55                  60

Pro Lys Asp Arg Arg Ser Thr Gly Lys Ser Trp Gly Lys Pro Gly Tyr
 65                  70                  75                  80

Pro Trp Pro Leu Tyr Gly Asn Glu Gly Leu Gly Trp Ala Gly Trp Leu
                85                  90                  95

Leu Ser Pro Arg Gly Ser Arg Pro Ser Trp Gly Pro Asn Asp Pro Arg
                100                 105                 110

His Arg Ser Arg Asn Val Gly Lys Val Ile Asp Thr Leu Thr Cys Gly
            115                 120                 125

Phe Ala Asp Leu Met Gly Tyr Ile Pro Val Val Gly Ala Pro Leu Gly
            130                 135                 140

Gly Val Ala Arg Ala Leu Ala His Gly Val Arg Val Leu Glu Asp Gly
145                 150                 155                 160

Val Asn Phe Ala Thr Gly Asn Leu Pro Gly Cys Ser Phe Ser Ile Phe
                165                 170                 175

Leu Leu Ala Leu Leu Ser Cys Ile Thr Thr Pro Val Ser Ala
                180                 185                 190

<210> SEQ ID NO 9
<211> LENGTH: 189
<212> TYPE: PRT
<213> ORGANISM: Hepatitis C Virus 3

<400> SEQUENCE: 9

Ser Thr Leu Pro Lys Pro Gln Arg Lys Thr Lys Arg Asn Thr Ile Arg
1               5                   10                  15

Arg Pro Gln Asp Val Lys Phe Pro Gly Gly Gly Gln Leu Val Gly Gly
            20                  25                  30

Val Tyr Val Leu Pro Arg Arg Gly Pro Arg Leu Gly Val Arg Ala Thr
                35                  40                  45

Arg Lys Thr Ser Glu Arg Ser Gln Pro Arg Gly Arg Arg Gln Pro Ile
 50                  55                  60

Pro Lys Ala Arg Arg Ser Glu Gly Arg Ser Trp Ala Gln Pro Gly Tyr
 65                  70                  75                  80

Pro Trp Pro Leu Tyr Gly Asn Glu Gly Cys Gly Trp Ala Gly Trp Leu
                85                  90                  95

Leu Ser Pro Arg Gly Ser Arg Pro Ser Trp Gly Pro Asn Asp Pro Arg
                100                 105                 110

Arg Arg Ser Arg Asn Leu Gly Lys Val Ile Asp Thr Leu Thr Cys Gly
            115                 120                 125

Phe Ala Asp Leu Met Gly Tyr Ile Pro Leu Val Gly Ala Pro Val Gly
            130                 135                 140

Gly Val Ala Arg Ala Leu Ala His Gly Val Arg Ala Leu Glu Asp Gly
145                 150                 155                 160

Ile Asn Phe Ala Thr Gly Asn Leu Pro Gly Cys Ser Phe Ser Ile Phe
                165                 170                 175

Leu Leu Ala Leu Phe Ser Cys Leu Ile His Pro Ala Ala
                180                 185

<210> SEQ ID NO 10
<211> LENGTH: 76

```
<212> TYPE: PRT
<213> ORGANISM: West Nile Virus

<400> SEQUENCE: 10

Arg Val Leu Ser Leu Thr Gly Leu Lys Arg Ala Met Leu Ser Leu Ile
1               5                   10                  15

Asp Gly Arg Gly Pro Thr Arg Phe Val Leu Ala Leu Leu Ala Phe Phe
            20                  25                  30

Arg Phe Thr Ala Ile Ala Pro Thr Arg Ala Val Leu Asp Arg Trp Arg
        35                  40                  45

Ser Val Asn Lys Gln Thr Ala Met Lys His Leu Leu Ser Phe Lys Lys
    50                  55                  60

Glu Leu Gly Thr Leu Thr Ser Ala Ile Asn Arg Arg
65                  70                  75

<210> SEQ ID NO 11
<211> LENGTH: 123
<212> TYPE: PRT
<213> ORGANISM: West Nile Virus

<400> SEQUENCE: 11

Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30

Ala Met Leu Ser Leu Ile Asp Gly Lys Gly Pro Ile Arg Phe Val Leu
        35                  40                  45

Ala Leu Leu Ala Phe Phe Arg Phe Thr Ala Ile Ala Pro Thr Arg Ala
    50                  55                  60

Val Leu Asp Arg Trp Arg Gly Val Asn Lys Gln Thr Ala Met Lys His
65                  70                  75                  80

Leu Leu Ser Phe Lys Lys Glu Leu Gly Thr Leu Thr Ser Ala Ile Asn
                85                  90                  95

Arg Arg Ser Ser Lys Gln Lys Lys Arg Gly Gly Lys Thr Gly Ile Ala
            100                 105                 110

Val Met Ile Gly Leu Ile Ala Ser Val Gly Ala
            115                 120

<210> SEQ ID NO 12
<211> LENGTH: 98
<212> TYPE: PRT
<213> ORGANISM: West Nile Virus

<400> SEQUENCE: 12

Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30

Ala Met Leu Ser Leu Ile Asp Gly Lys Gly Pro Ile Arg Phe Val Leu
        35                  40                  45

Ala Leu Leu Ala Ala Pro Thr Arg Ala Val Leu Asp Arg Trp Arg Gly
    50                  55                  60

Val Asn Lys Gln Thr Ala Met Lys His Leu Leu Ser Phe Lys Lys Glu
65                  70                  75                  80

Leu Gly Thr Leu Thr Ser Ala Ile Asn Arg Arg Ser Ser Lys Gln Lys
                85                  90                  95

Lys Arg
```

<210> SEQ ID NO 13
<211> LENGTH: 68
<212> TYPE: PRT
<213> ORGANISM: West Nile Virus

<400> SEQUENCE: 13

Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30

Ala Met Leu Ser Leu Ile Asp Gly Lys Gly Pro Ile Arg Phe Val Leu
        35                  40                  45

Ala Leu Leu Gly Thr Leu Thr Ser Ala Ile Asn Arg Arg Ser Ser Lys
    50                  55                  60

Gln Lys Lys Arg
65

<210> SEQ ID NO 14
<211> LENGTH: 95
<212> TYPE: PRT
<213> ORGANISM: West Nile Virus

<400> SEQUENCE: 14

Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30

Ala Met Leu Ser Leu Ile Asp Gly Lys Gly Pro Phe Arg Phe Thr Ala
        35                  40                  45

Ile Ala Pro Thr Arg Ala Val Leu Asp Arg Trp Arg Gly Val Asn Lys
    50                  55                  60

Gln Thr Ala Met Lys His Leu Leu Ser Phe Lys Lys Glu Leu Gly Thr
65                  70                  75                  80

Leu Thr Ser Ala Ile Asn Arg Arg Ser Ser Lys Gln Lys Lys Arg
                85                  90                  95

<210> SEQ ID NO 15
<211> LENGTH: 69
<212> TYPE: PRT
<213> ORGANISM: West Nile Virus

<400> SEQUENCE: 15

Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30

Ala Met Leu Ser Leu Ile Glu Thr Ala Met Lys His Leu Leu Ser Phe
        35                  40                  45

Lys Lys Glu Leu Gly Thr Leu Thr Ser Ala Ile Asn Arg Arg Ser Ser
    50                  55                  60

Lys Gln Lys Lys Arg
65

<210> SEQ ID NO 16
<211> LENGTH: 57
<212> TYPE: PRT
<213> ORGANISM: West Nile Virus

<400> SEQUENCE: 16

```
Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30

Ala Met Leu Ser Leu Ile Glu Leu Gly Thr Leu Thr Ser Ala Ile Asn
        35                  40                  45

Arg Arg Ser Ser Lys Gln Lys Lys Arg
        50                  55
```

<210> SEQ ID NO 17
<211> LENGTH: 88
<212> TYPE: PRT
<213> ORGANISM: West Nile Virus

<400> SEQUENCE: 17

```
Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30

Ala Met Leu Ser Leu Ile Glu Leu Gly Thr Leu Thr Ser Ala Met Leu
        35                  40                  45

Lys Arg Gly Met Pro Arg Val Leu Ser Leu Ile Gly Leu Lys Arg Ala
    50                  55                  60

Met Leu Ser Leu Ile Glu Leu Gly Thr Leu Thr Ser Ala Ile Asn Arg
65                  70                  75                  80

Arg Ser Ser Lys Gln Lys Lys Arg
                85
```

<210> SEQ ID NO 18
<211> LENGTH: 76
<212> TYPE: PRT
<213> ORGANISM: West Nile Virus

<400> SEQUENCE: 18

```
Arg Val Leu Ser Leu Ile Gly Leu Lys Arg Ala Met Leu Ser Leu Ile
1               5                   10                  15

Asp Gly Lys Gly Pro Ile Arg Phe Val Leu Ala Leu Leu Ala Phe Phe
            20                  25                  30

Arg Phe Thr Ala Ile Ala Pro Thr Arg Ala Val Leu Asp Arg Trp Arg
        35                  40                  45

Gly Val Asn Lys Gln Thr Ala Met Lys His Leu Leu Ser Phe Lys Lys
    50                  55                  60

Glu Leu Gly Thr Leu Thr Ser Ala Ile Asn Arg Arg
65                  70                  75
```

<210> SEQ ID NO 19
<211> LENGTH: 66
<212> TYPE: PRT
<213> ORGANISM: West Nile Virus

<400> SEQUENCE: 19

```
Arg Val Leu Ser Leu Ile Gly Leu Lys Arg Ala Met Leu Ser Leu Ile
1               5                   10                  15

Asp Gly Lys Gly Pro Phe Arg Phe Thr Ala Ile Ala Pro Thr Arg Ala
            20                  25                  30

Val Leu Asp Arg Trp Arg Gly Val Asn Lys Gln Thr Ala Met Lys His
        35                  40                  45

Leu Leu Ser Phe Lys Lys Glu Leu Gly Thr Leu Thr Ser Ala Ile Asn
    50                  55                  60
```

```
Arg Arg
 65

<210> SEQ ID NO 20
<211> LENGTH: 39
<212> TYPE: PRT
<213> ORGANISM: West Nile Virus

<400> SEQUENCE: 20

Arg Val Leu Ser Leu Ile Gly Leu Lys Arg Ala Met Leu Ser Leu Ile
1               5                   10                  15

Thr Ala Met Lys His Leu Leu Ser Phe Lys Lys Glu Leu Gly Thr Leu
            20                  25                  30

Thr Ser Ala Ile Asn Arg Arg
        35

<210> SEQ ID NO 21
<211> LENGTH: 69
<212> TYPE: PRT
<213> ORGANISM: West Nile Virus

<400> SEQUENCE: 21

Arg Val Leu Ser Leu Ile Gly Leu Lys Arg Ala Met Leu Ser Leu Ile
1               5                   10                  15

Asp Gly Lys Gly Pro Ile Arg Phe Val Leu Ala Leu Ala Ala Pro
            20                  25                  30

Thr Arg Ala Val Leu Asp Arg Trp Arg Gly Val Asn Lys Gln Thr Ala
        35                  40                  45

Met Lys His Leu Leu Ser Phe Lys Lys Glu Leu Gly Thr Leu Thr Ser
    50                  55                  60

Ala Ile Asn Arg Arg
 65

<210> SEQ ID NO 22
<211> LENGTH: 39
<212> TYPE: PRT
<213> ORGANISM: West Nile Virus

<400> SEQUENCE: 22

Arg Val Leu Ser Leu Ile Gly Leu Lys Arg Ala Met Leu Ser Leu Ile
1               5                   10                  15

Asp Gly Lys Gly Pro Ile Arg Phe Val Leu Ala Leu Leu Gly Thr Leu
            20                  25                  30

Thr Ser Ala Ile Asn Arg Arg
        35

<210> SEQ ID NO 23
<211> LENGTH: 84
<212> TYPE: PRT
<213> ORGANISM: West Nile Virus

<400> SEQUENCE: 23

Asn Met Leu Lys Arg Gly Met Pro Arg Val Leu Ser Leu Ile Gly Leu
1               5                   10                  15

Lys Arg Ala Met Leu Ser Leu Ile Asp Gly Lys Gly Pro Ile Arg Phe
            20                  25                  30

Val Leu Ala Leu Leu Ala Phe Phe Arg Phe Thr Ala Ile Ala Pro Thr
        35                  40                  45

Arg Ala Val Leu Asp Arg Trp Arg Gly Val Asn Lys Gln Thr Ala Met
    50                  55                  60
```

```
<210> SEQ ID NO 24
<211> LENGTH: 85
<212> TYPE: PRT
<213> ORGANISM: Dengue Virus

<400> SEQUENCE: 24

Asn Met Leu Lys Arg Glu Arg Asn Arg Val Ser Thr Val Gln Gln Leu
1               5                   10                  15

Thr Lys Arg Phe Ser Leu Gly Met Leu Gln Gly Arg Gly Pro Leu Lys
                20                  25                  30

Leu Phe Met Ala Leu Val Ala Phe Leu Arg Phe Leu Thr Ile Pro Pro
            35                  40                  45

Thr Ala Gly Ile Leu Lys Arg Trp Gly Thr Ile Lys Lys Ser Lys Ala
        50                  55                  60

Ile Asn Val Leu Arg Gly Phe Arg Lys Glu Ile Gly Arg Met Leu Asn
65                  70                  75                  80

Ile Leu Asn Arg Arg
                85
```

Preceding sequence ending:
```
Lys His Leu Leu Ser Phe Lys Lys Glu Leu Gly Thr Leu Thr Ser Ala
65                  70                  75                  80

Ile Asn Arg Arg
```